(12) United States Patent
Jordan et al.

(10) Patent No.: US 8,084,232 B2
(45) Date of Patent: Dec. 27, 2011

(54) **POLYNUCLEOTIDES ENCODING *PAPIO CYNOCEPHALUS* TOLL-LIKE RECEPTOR 3**

(75) Inventors: Jarrat Jordan, Radnor, PA (US); Jessica Schreiter, Radnor, PA (US); Bethany Swencki-Underwood, Radnor, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 71 days.

(21) Appl. No.: 12/570,358

(22) Filed: Sep. 30, 2009

(65) Prior Publication Data

US 2010/0086487 A1 Apr. 8, 2010

Related U.S. Application Data

(60) Provisional application No. 61/102,375, filed on Oct. 3, 2008.

(51) Int. Cl.
*C12N 15/64* (2006.01)
*C12N 15/24* (2006.01)
*C12P 21/02* (2006.01)

(52) U.S. Cl. .................. 435/69.52; 435/320.1; 435/471; 435/325; 536/23.5; 530/351

(58) Field of Classification Search ........................ None
See application file for complete search history.

(56) References Cited

U.S. PATENT DOCUMENTS

| 5,543,131 A | 8/1996 | Levy |
| 2007/0072202 A1 | 3/2007 | Bates et al. |
| 2007/0098716 A1 | 5/2007 | Duffy et al. |
| 2007/0253982 A1 | 11/2007 | Song et al. |

OTHER PUBLICATIONS

Alexopoulou et al, Nature, 2001, vol. 413, pp. 732-738.*
Bell et al, PNAS, 2005, vol. 102, No. 31, pp. 10976-10980.*
Cho et al, Science, 2005, vol. 309, pp. 581-585.*
PCT International Search Report dated Mar. 16, 2010.
Dogusan, et al., "Double-Stranded RNA Induces Pancreatic β-Cell Apoptosis by Activation of the Toll-Like Receptor 3 and Interferon Regulatory Factor 3 Pathways," Diabetes, 57: 1236-1245 (2008).
Anthony Gaspari, "Innate and adaptive immunity and the pathophysiology of psoriasis," Journal of the American Academy of Dermatology, 54: S67-S80 (2006).
Hoffman, et al., "TLR-targeted therapeutics," Nature Review Drug Discovery, 4: 879-880 (2005).
Kanzler, et al., "Therapeutic targeting of innate immunity with Toll-like receptor agonists and antagonists," Nature Medicine, 13: 552-559 (2007).
Lancaster, et al., "The physiological regulation of toll-like receptor expression and function in humans," Journal of Physiology, 563: 945-955 (2005).
Loisel, et al., "Relevance, advantages and limitations of animal models used in the development of monoclonal antibodies for cancer treatment," Critical Reviews in Oncology/Hematology, 62: 34-42 (2007).
Le Goffic, et al., "Detrimental Contribution of the Toll-Like Receptor (TLR)3 to Influenza A Virus-Induced Acute Pneumonia," PloS Pathogens, 2: E53 (2006).
Pierre Miossec, "An update on the cytokine network in rheumatoid arthritis," Current Opinion in Rheumatology, 16: 218-222 (2004).
Ogata, et al., "Cytokine and Anti-cytokine Therapies for Inflammatory Bowel Disease," Current Pharmaceutical Design, 9: 1107-1113 (2003).
Picha, et al., "Protein Engineering Strategies for Sustained Glucagon-Like peptide-1 Receptor-Dependent Control of Glucose Homeostasis," Diabetes, 57: 1926-1934 (2008).
Nina Rezaei, "Therapeutic targeting of pattern-recognition receptors," International Immunopharmacology, 6: 863-869 (2006).
Francois Romagne, "Current and future drugs targeting one class of innate immunity receptors: the Toll-like receptors," Drug Discovery Today, 12(1/2): 80-87 (2007).
Stumpp, et al., "DARPins: A true alternative to antibodies," Current Opinion in Drug Discovery & Development, 10(2): 153-159 (2007).
Tabeta, et al., "Toll-like receptors 9 and 3 as essential components of innate immune defense against mouse cytomegalovirus infection," Proceedings of the National Academy of Science USA, 101: 3516-3521 (2004).
Takeda, et al., "Microbial recognition by Toll-like receptors," Journal of Dermatological Science, 34: 73-82 (2004).
Takii, et al., "Enhanced expression of type 1 interferon and toll-like receptor-3 in primary biliary cirrhosis," Laboratory Investigations, 85: 908-920 (2005).
David M. Underhill, "Toll-like receptors and microbes take aim at each other," Current Opinion in Immunology, 16: 483-487 (2004).
Van Amersfoort, et al., "Receptors, Mediators, and Mechanisms Involved in Bacterial Sepsis and Septic Shock," Clinical Microbiology Reviews, 16(3): 379-414 (2003).
Ingrid Wickelgren, "Targeting the Tolls," Science, 312: 184-187 (2006).
Zhou, et al., "Recognition of Double-Stranded RNA by TLR3 Induces Severe Small Intestinal Injury in Mice," Journal of Immunology, 178: 4548-4556 (2007).

* cited by examiner

*Primary Examiner* — Bridget E Bunner
*Assistant Examiner* — Fozia Hamud
(74) *Attorney, Agent, or Firm* — Kirk Baumeister

(57) ABSTRACT

Isolated polynucleotides encoding *Papio cynocephalus* Toll-Like Receptor 3 (Baboon TLR3), polypeptides obtainable from expression of these polynucleotides, recombinant cells, and methods of use are disclosed.

13 Claims, 4 Drawing Sheets

Figure 1A

```
human  TLR3      (1)  MRQTLPCIYFWGGLLPFGMLCASSTTKCTVSHEVADCSHLKLTQVPDDLP
baboon TLR3      (1)  MRQTLPYIYFWWGLLPFGMLCASSTNKCTVSQEVADCSHLKLTQVPDDLP human  TLR3     (51)  TNITVLNLTHNQLRRLPAANFTRYSQLTSLDVGFNTISKLEPELCQKLPM
baboon TLR3     (51)  TNITVLNLTHNQLRRLPAANFTRYSQLTILDVGFNSISKLEPELCQKLPM human  TLR3    (101)  LKVLNLQHNELSQLSDKTFAFCTNLTELHLMSNSIQKIKNNPFVKQKNLI
baboon TLR3    (101)  LKVLNLQHNELSQLSDKTFAFCTNLTELHLMSNSIQKIKSNPFVKQKNLI human  TLR3    (151)  TLDLSHNGLSSTKLGTQVQLENLQELLLSNNKIQALKSEELDIFANSSLK
baboon TLR3    (151)  TLDLSHNGLSSTKLGTQVQLENLQELLLSNNKIQALKSEELDILANSSLK human  TLR3    (201)  KLELSSNQIKEFSPGCFHAIGRLFGLFLNNVQLGPSLTEKLCLELANTSI
baboon TLR3    (201)  KLELSSNQIKEFSPGCFHAIGRLLGLFLNNVQLGPSLTEKLCLELANTSI human  TLR3    (251)  RNLSLSNSQLSTTSNTTFLGLKWTNLTMLDLSYNNLNVVGNDSFAWLPQL
baboon TLR3    (251)  RNLSLSNSQLSTTSNTTFLGLKWTNLTMLDLSHNNLNVIGNDSFVWLPHL human  TLR3    (301)  EYFFLEYNNIQHLFSHSLHGLFNVRYLNLKRSFTKQSISLASLPKIDDFS
baboon TLR3    (301)  EYFFLEYNNIQHLLSHSLHGLFNVRYLNLKRSFTKQSISLASLPKIDDFS human  TLR3    (351)  FQWLKCLEHLNMEDNDIPGIKSNMFTGLINLKYLSLSNSFTSLRTLTNET
baboon TLR3    (351)  FQWLTCLEHLNMEDNDISGIKSNMFTGLINLKYLSLSNSFTSLQTLTNET human  TLR3    (401)  FVSLAHSPLHILNLTKNKISKIESDAFSWLGHLEVLDLGLNEIGQELTGQ
baboon TLR3    (401)  FVSLAHSPLHILNLTKNKISKIESGAFSWLGHLEVLDLGLNEIGQELTGQ human  TLR3    (451)  EWRGLENIFEIYLSYNKYLQLTRNSFALVPSLQRLMLRRVALKNVDSSPS
baboon TLR3    (451)  EWSGLENIFEIYLSYNKYLQLTKNSFALVRSLQRLMLRRVALKNVDCSPS human  TLR3    (501)  PFQPLRNLTILDLSNNNIANINDDMLEGLEKLEILDLQHNNLARLWKHAN
baboon TLR3    (501)  PFQPLGNLTILDLSNNNIANINDDMLEGLEKLEILDLQHNNLARLWKHAN human  TLR3    (551)  PGGPIYFLKGLSHLHILNLESNGFDEIPVEVFKDLFELKIIDLGLNNLNT
baboon TLR3    (551)  PGGPVYFLKGLSHLHILNLESNGFDEIPVEVFKDLSELKIIDLGLNNLNT human  TLR3    (601)  LPASVFNNQVSLKSLNLQKNLITSVEKKVFGPAFRNLTELDMRFNPFDCT
baboon TLR3    (601)  LPESVFDNQVSLKSLNLQKNLITSVEKKVFGPAFRNLSNLDMRFNPFDCT human  TLR3    (651)  CESIAWFVNWINETHTNIPELSSHYLCNTPPHYHGFPVRLFDTSSCKDSA
baboon TLR3    (651)  CESIAWFVNWINKTHANIPELSSHYLCNTPPHYHGFPVRLFDTSSCKDSA human  TLR3    (701)  PFELFFMINTSILLIFIFIVLLIHFEGWRISFYWNVSVHRVLGFKEIDRQ
baboon TLR3    (701)  PFELLFMINTSILLIFIFVVLLIHFEGWRISFYWNVSVHRVLGFREIDRQ human  TLR3    (751)  TEQFEYAAYIIHAYKDKDWVWEHFSSMEKEDQSLKFCLEERDFEAGVFEL
baboon TLR3    (751)  TEQFEYAAYIIHAHKDKDWVWEHFSSMEKEDQSLKFCLEERDFEAGVFEL
```

Figure 1B

```
human TLR3   (801) EAIVNSIKRSRKIIFVITHHLLKDPLCKRFKVHHAVQQAIEQNLDSIILV
baboon TLR3  (801) EAIVNSIKRSRKIIFIITHHLLKDPLCKRFKVHHAVQQAIEQNLDPIILI human TLR3   (851) FLEEIPDYKLNHALCLRRGMFKSHCILNWPVQKERIGAFRHKLQVALGSK
baboon TLR3  (851) FLEEIPDYKLNHALCLRRGMFKSHCILNWPVQKERIGAFHHKLQVALGSK human TLR3   (901) NSVH-
baboon TLR3  (901) NSVH-
```

POLYNUCLEOTIDES ENCODING *PAPIO CYNOCEPHALUS* TOLL-LIKE RECEPTOR 3

CROSS-REFERENCE TO RELATED APPLICATIONS

This application claims priority to U.S. Provisional Application Ser. No. 61/102,375, filed 3 Oct. 2008, the entire contents of which is incorporated herein by reference in its entirety.

FIELD OF THE INVENTION

The present invention relates to *Papio cynocephalus* (Yellow Baboon) Toll-Like Receptor 3 and its uses.

BACKGROUND OF THE INVENTION

Toll-like receptors (TLRs) regulate activation of the innate immune response and influence the formation of adaptive immunity by detecting and initiating signal transduction cascades in response to bacterial, viral, parasitic, and in some cases host-derived ligands (Lancaster et al., J. Physiol. 563: 945-55, 2005). Members of the TLR family TLR1, TLR2, TLR4 and TLR6 are located on the plasma membrane and activate downstream signaling pathways in response to ligands including protein or lipid components of bacteria and fungi. TLR3, TLR7 and TLR9 are preferentially localized intracellularly, and respond to dsRNA, ssRNA and unmethylated CpG DNA, respectively.

TLRs signal through adaptor molecules myeloid differentiation factor 88 (MyD88), Toll/IL-1 receptor domain containing adaptor inducing interferon-beta (TRIF) and TRIF-related adaptor molecule (TRAM), initiating signaling pathways involving JNK/p38 kinase, interferon-regulatory factors (IFN) IFN-3, IFN-5 and IFN-7, and NF-kB, leading to the production of pro-inflammatory cytokines (Romagne, Drug Discov. Today 12:80-87, 2007). Dysregulation of TLR signaling is believed to cause a multitude of problems, and therapeutic strategies are in development towards this axis (Hoffman et al., Nat. Rev. Drug Discov. 4:879-880, 2005; Rezaei, Int. Immunopharmacol. 6:863-869, 2006; Wickelgren, Science 312:184-187, 2006). For example, antagonists of TLRs4, 7 and 9 are in clinical development for severe sepsis and lupus, (Kanzler et al. Nat. Med. 13:552-559, 2007).

TLR3 signaling is activated by dsRNA, mRNA or RNA released from necrotic cells upon inflammation or virus infection, and results in the induced secretion of interferons and pro-inflammatory cytokines, which have been associated with pathogen infections, and shown to contribute to a spectrum of inflammatory, immune-mediated and autoimmune diseases, for example colitis, asthma, psoriasis, septic shock, rheumatoid arthritis, inflammatory bowl disease and type I diabetes (Tabeta et al., Proc. Natl. Acad. Sci. 101:3516-3521, 2004; Underhill, Curr. Opin. Immunol. 16:483-487, 2004; Gaspari, J. Am. Acad. Dermatol. 54:S67-80, 2006; Van Amersfoort et al., Clin. Microbiol. Rev. 16:379-414, 2003; Miossec et al., Curr. Opin. Rheumatol. 16:218-222, 2004; Ogata and Hibi, Curr. Pharm. Res. 9:1107-1113, 2003; Takeda and Akira, J. Derm. Sci. 34:73-82, 2004; Doqusan et al. Diabetes 57:1236-1245, 2008). TLR3 expression has been shown to correlate with inflammatory responses associated with pathological conditions such as primary biliary cirrhosis of liver tissues (Takii et al., Lab Invest. 85:908-920, 2005). TLR3 also plays a key role in the immune responses upon virus infections; for example, TLR3 deficient animals display significantly reduced inflammatory mediators and a survival advantage over wild type animals upon influenza A virus infection (Le Goffic et al., PloS Pathog. 2:e53, 2006), and TLR3 deficient animals are protected from rotavirus infection-induced mucosal epithelial breakdown (Zhou et al. J. Immunology 178:4548-4556, 2007). In necrotic conditions, the release of intracellular content, including TLR3 ligand endogenous mRNA triggers inflammation expression of cytokines, chemokines and other factors to facilitate clearance of dead cell remnants and repair the damage. Necrosis often perpetuates chronic or aberrant inflammatory processes leading to secondary damage or cascade of effects.

Currently, a number of different approaches have been taken to target the activity of TLR3 for treatment of different indications. These approaches include TLR3 modulators such as agonists and antagonists, antibodies, peptides, TLR3 ligands dsRNA and poly(I:C), as well as functional analogs of these that target TLR3 activity. The potential indications for TLR3 antagonists include inflammatory conditions, sepsis, inflammatory bowel disease, inflammatory pulmonary disease, and autoimmune diseases. The potential indications and uses for TLR3 agonists include post-viral fatigue syndrome, glioma, prostate cancer, antiviral vaccines, bladder cancer, cervical dysplasia, human papilloma virus infection, breast cancer, viral infection prevention, tissue regeneration, and avian influenza vaccines.

Predictive pharmacokinetic, safety and efficacy studies will be required before any TLR3 modulator for human use can be brought to the market place. Such studies will involve both in vitro and in vivo testing in animal models of TLR3-associated pathologies. Lack of cross-reactivity of the modulators with TLR3s across species can pose a challenge in these studies. Thus, use of for example antibody-based TLR3 modulators may require evaluation of cross-reactivity of the antibodies between species, generation of surrogate antibodies against a TLR3 polypeptide expressed by a particular model animal, as well as significant in vitro characterization of such surrogate antibodies. Evaluation of cross-reactivity, surrogate generation and in vitro characterization will require the use of TLR3 polynucleotides and polypeptides from a suitable model animal. Importantly, the identification of suitable animal models for the above-mentioned studies requires the identification of animal species expressing TLR3 with high identity and homology to human TLR3.

Thus, a need exists for the identification of polynucleotides encoding TLR3 and TLR3 polypeptides being expressed in an animal model identified as suitable for the predictive pharmacokinetic, safety and efficacy studies of TLR3 modulators. A need also exists for related methods such as methods of expressing such polypeptides and testing the cross-reactivity of TLR3 modulators.

BRIEF DESCRIPTION OF THE DRAWINGS

FIGS. 1A and 1B. Protein sequence alignment of *Papio cynocephalus* vs. human TLR3.

SUMMARY OF THE INVENTION

Figure 2:
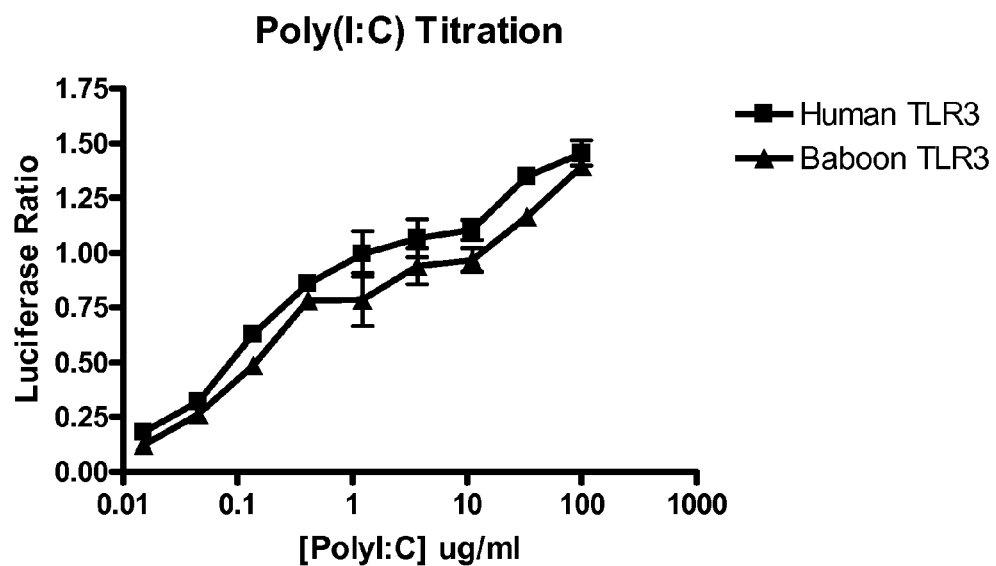
FIG. 2. Dose-dependent NF-κB activation through human and *Papio cynocephalus* TLR3 proteins by poly(I:C).

One aspect of the invention is an isolated polynucleotide encoding a polypeptide comprising the amino acid sequence shown in SEQ ID NO: 7.

Another aspect of the invention is an isolated polynucleotide encoding a polypeptide comprising the amino acid sequence shown in SEQ ID NO: 8.

Another aspect of the invention is an isolated polynucleotide encoding a polypeptide comprising the amino acid sequence shown in SEQ ID NO: 9.

Another aspect of the invention is an isolated polynucleotide encoding a polypeptide comprising the amino acid sequence shown in SEQ ID NO: 10.

Another aspect of the invention is a vector comprising an isolated polynucleotide having the sequence shown in SEQ ID NO: 1, 2, 3, 4, 5 or 6.

Another aspect of the invention is an isolated polypeptide comprising a polypeptide having the sequence shown in SEQ ID NO: 7.

Another aspect of the invention is an isolated polypeptide comprising a polypeptide having the sequence shown in SEQ ID NO: 8.

Another aspect of the invention is an isolated polypeptide comprising a polypeptide having the sequence shown in SEQ ID NO: 9.

Another aspect of the invention is an isolated polypeptide comprising a polypeptide having the sequence shown in SEQ ID NO: 10.

Another aspect of the invention is a method for expressing a polypeptide of the invention.

Another aspect of the invention is an isolated antibody that specifically binds a polypeptide of the invention.

Another aspect of the invention is methods for determining cross-reactivity of a human TLR3 modulator with *Papio cynocephalus* TLR3.

Another aspect of the invention is a method of assessing the safety of a TLR3 modulator for use in humans.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a polypeptide" is a reference to one or more polypeptides and includes equivalents thereof known to those skilled in the art.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The present invention provides isolated Yellow Baboon (*Papio cynocephalus*) Toll-Like Receptor 3 (baboon TLR3) polynucleotides, vectors comprising these polynucleotides, isolated host cells, polypeptides obtainable from expression of these polynucleotides, methods for expressing the polypeptides of the invention, and methods of using the polynucleotides and polypeptides of the invention.

TLR3 recognizes dsRNA or endogenous mRNA either present in the genome of many viruses, produced during viral replication or released by necrotic cells. Upon ligand binding to TLR3, signal transduction is initiated which leads to the activation of NF-kB and IRF-3, resulting in the production of pro- and anti-inflammatory cytokines in addition to type 1 interferons. These signals act on surrounding cells to alert other components of the immune system that an infection is present. In some instances, a dysregulation of this innate immune response can lead to an excess of inflammatory mediators and therefore, can exacerbate many chronic diseases such as asthma, COPD, ulcerative colitis, rheumatoid arthritis and osteoarthritis.

Sustained TLR3 activation is a critical component in the modulation of infection-associated inflammatory diseases. Thus, development of immunomodulatory therapies from a pharmaceutical perspective, may be a way of controlling inflammation and hence, returning innate immune function back to homeostatic.

The compositions and methods of the invention can be used for a variety of specific applications. The polynucleotides and vectors of the invention are useful because they encode Yellow Baboon (*Papio cynocephalus*) TLR3 (baboon TLR3) polypeptides and can be used to express these polypeptides. These baboon TLR3 polypeptides are, in turn, useful because they can be used to increase or control antiviral responses after exposure to dsRNA or other TLR3 ligands when they are recombinantly overexpressed or introduced by other means into a host animal or tissue. The full-length baboon TLR3 polypeptide sequence of the invention (SEQ ID NO: 10) is 95.7% identical, and 96.8% similar to the human TLR3 polypeptide (SEQ ID NO: 13), allowing predictive pharmacokinetic, safety and efficacy studies of TLR3 therapeutics, and other uses.

Polypeptides comprising the extracellular domain of baboon TLR3 can also be used as ligand sink-type antagonists that bind available TLR3 ligands or TLR3 associated proteins necessary for TLR3 activation and thus control TLR3 activity. Baboon TLR3 polypeptides can also be used to generate therapeutic antibodies for the positive or negative modulation of the activity of baboon TLR3 or TLR3s from other sources. Baboon TLR3 polypeptides can also be used in in vitro or in vivo assays to identify other therapeutics such as small molecules, oligonucleotides or peptides capable of modulating the activity of baboon TLR3 or other TLR3s. The methods of expression disclosed are useful because these methods permit the expression of baboon TLR3 peptides. Other methods disclosed are useful for assessing safety and cross-reactivity between species of a TLR3 therapeutic.

The term "polynucleotide" means a molecule comprising a chain of nucleotides covalently linked by a sugar-phosphate backbone or other equivalent covalent chemistry. Double and single stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence. Typically, such "complementary sequences" are capable of forming a double-stranded polynucleotide molecule such as double-stranded DNA or double-stranded RNA when combined under appropriate conditions with the first isolated polynucleotide sequence.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The term "polypeptide" means a molecule that comprises at least two amino acid residues linked by a peptide bond to form a polypeptide. Small polypeptides of less than 50 amino acids may be referred to as "peptides". Polypeptides may also be referred as "proteins."

The term "antibody" refers to a molecule specifically binding to an antigen, and includes dimeric, trimeric and multimeric antibodies, and chimeric, humanized and fully human antibodies. Also, an antibody may be a whole antibody or a functional fragment of an antibody molecule, such as a fragment retaining at least its antigen binding function, and include Fab, F(ab'), F(ab')$_2$, scFv, dsFv, and diabodies. For example, antibody fragments may be obtained using proteolytic enzymes (e.g., a whole antibody is digested with papain to produce Fab fragments, and pepsin treatment results in the production of F(ab')$_2$ fragments). Techniques for the preparation and use of the various antibodies are well known in the art (Ausubel, et al., ed., Current Protocols in Molecular Biology, John Wiley & Sons, Inc., NY 1987-2001; Sambrook, et al., Molecular Cloning: A Laboratory Manual, $2^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, N.Y., 1997-2001; Kohler et al., Nature 256:495-497, 1975; U.S. Pat. No. 4,816,567, Queen et al., Proc. Natl. Acad. Sci. 86:10029-10033, 1989). For example, fully human monoclonal antibodies lacking any non-human sequences can be prepared from human immunoglobulin transgenic mice or from phage display libraries (Lonberg et al., Nature 368:856-859, 1994; Fishwild et al., Nature Biotech. 14:845-851, 1996; Mendez et al., Nature Genetics 15:146-156, 1997; Knappik et al., J. Mol. Biol. 296:57-86, 2000; Krebs et al., J. Immunol. Meth. 265:67-84, 2001).

An antibody molecule or preparation "specifically binds" a given antigen when it binds this antigen with higher affinity and in a specific, as opposed to non-specific fashion, relative to a second non-identical antigen. Stated differently, the "specific binding" of an antibody molecule or preparation can be used to distinguish between two different polypeptides.

A "fragment" is a polypeptide having an amino acid sequence that comprises a portion, but not all, of any amino acid sequence of any polypeptide of the invention. Fragments can include, for example, truncated polypeptide having a portion of an amino acid sequence corresponding to a signal peptide, extracellular domain, transmembrane domain, or cytoplasmic domain, or variants thereof, such as a continuous series of residues that includes a heterologous amino- and/or carboxy-terminal amino acid sequence. Degradation forms of the polypeptides of the invention produced by, or in, a host cell are also included. Other exemplary fragments are characterized by structural or functional attributes such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions and high antigenic index regions. Importantly, the polypeptides of the invention can be used or provided as fragments.

A "variant polypeptide" is a second polypeptide in which amino acid substitutions, insertions, deletions or combinations thereof have been made relative to a first polypeptide. Naturally occurring, modified or atypical amino acids can be used for substitutions and insertions.

A "variant polynucleotide" is a second polynucleotide in which nucleic acid residue substitutions, insertions, deletions, or combinations thereof have been made relative to a first polynucleotide sequence. Naturally occurring or modified nucleobases can be used for substitutions and deletions.

The term "modulator" means a molecule or preparation that is believed to provide a therapeutic benefit in humans or other animals and is believed to provide that therapeutic benefit, in part, through activating or suppressing TLR3. Such TLR3s may comprise the polypeptides of the invention. Examples of TLR3 therapeutics include known TLR3 ligands such as dsRNA or poly(I:C) or an anti-TLR3 antibody, which bind and activate or inhibit TLR3 to produce the therapeutic benefits of increased or decreased antiviral activity and immune system stimulation.

The term "deleterious symptom" means any symptom presented by an animal that indicates harm to the animal has occurred.

The term "cross-reactivity" means binding of a second antigen to an antibody that was generated against the first antigen. Cross-reactivity usually occurs when antigens are derived from polypeptides of different species, or from polypeptides belonging to a protein family. Cross-reactivity can be the binding of an antibody generated against human TLR3 to a baboon TLR3 polypeptide.

The term "modulator" includes inhibitors and activators. Inhibitors are agents that bind to, partially or totally block stimulation, decrease, prevent, delay activation, inactivate, desensitize, or down regulate the activity of TLR3, e.g., antagonists. Activators are agents that bind to, stimulate, increase, open, activate, facilitate, enhance activation, sensitize or up regulate the activity of TLR3, e.g., agonists. Modulators include antibodies, antibody portions or fragments, peptides, polypeptides, oligonucleotides, small chemical molecules and the like. Known TLR3 modulators are for example poly(I:C) and ODN2006 (Alexopoulou et al., Nature 413:732-738, 2001; Ranjith-Kumar et al., Mol Cell Biol. 28:4507-19, 2008). Assays for modulators include applying putative modulator compounds to a cell expressing a TLR3 and then determining the functional effects on TLR3 signaling, as described below.

As used herein, the term "modulation of TLR3 activity" means inhibiting, suppressing, partially or totally blocking stimulation, decreasing, preventing, delaying activation, inactivating, desensitizing, down regulating the activity of TLR3 signaling, activating, facilitating, enhancing activation, sensitizing, or up regulating the activity of TLR3. Inhibition of Toll-like receptor activity is achieved when the Toll-like receptor activity value relative to the control is 50-80%, optionally 25-50% or 0-25%. Activation of Toll-like receptor activity is achieved when Toll-like receptor activity value relative to the control is 100-125%, optionally 125-150% or 150-1800, where control samples are assigned a relative TLR3 activity value of 100%. As discussed above methods of measuring TLR3 activity and an effect of a molecule, for example TLR3 therapeutic or antibody on TLR3 activity may be evaluated using any suitable technique known in the art.

The term "TLR3 activity" or "activity" can be measured in a number of possible systems based upon a TLR3 signal transduction pathway. Determination of TLR3 activity is based on the use of native genes or, alternatively, transfected or otherwise artificially introduced reporter gene constructs that are responsive to the TLR3 signal transduction pathway. Reporter genes and reporter gene constructs useful for the assays include a reporter gene operatively linked to a promoter sensitive to NF-κB. Examples of such promoters include those for IL-6, IL-8 and IL-12 p40 (Murphy et al., Mol. Cell. Biol. 15:5258-5267, 1995; Libermann and Baltimore, Mol. Cell. Biol. 10:2327-2334, 1990; Mauviel et al., J. Immunol. 149:2969-2976, 1992). The reporter gene operatively linked to the TLR3-sensitive promoter can include, for example, luciferase, alkaline phosphatase, β-galactosidase, chloramphenicol acetyltransferase (CAT), or green-fluorescent protein (GFP). An exemplary TLR3 activity assay uses a reporter gene assay for TLR3 based on NF-κB activation induced by a poly(I:C) ligand. This assay has been established and is commonly used by practitioners in the field (Alexopoulos et al., Nature 413: 732-738, 2001; Häcker et al., EMBO J. 18:6973-6982, 1999). Intracytoplasmic signaling events resulting from TLR3 activation that can be detected include activation of p38, extracellular signal-regulated kinase (ERK), and c-jun N-terminal kinase (JNK) pathways, Ikappa B kinase phosphorylation and activation or degradation of Iκα or Iκβ, and nuclear translocation of NF-κB. The effects of TLR3 can also be monitored by assessing the amount of cytokines and chemokines produced upon induction with a TLR3 ligand such as poly(I:C), for example IFN-γ, IL-6, IL-12, TNF-α, macrophage inflammatory protein-1 alpha (MIP1-α) IL-1α, IP-10, and MIG (Kabelitz, Curr. Opin. Immunol. 19:39-45, 2007). Secreted molecules can be assayed using enzyme-linked immunosorbent assay (ELISA) or bioassays. These and other suitable readout systems are well known in the art and are commercially available.

One aspect of the invention is an isolated polynucleotide comprising a polynucleotide having the sequence shown in SEQ ID NO: 1 or a complementary sequence thereof. The polynucleotide sequence shown in SEQ ID NO: 1 encodes a polypeptide comprising the predicted mature form of the extracellular domain of baboon TLR3.

Another aspect of the invention is an isolated polynucleotide comprising a polynucleotide having the sequence shown in SEQ ID NO: 2 or a complementary sequence thereof. The polynucleotide sequence shown in SEQ ID NO: 2 encodes a polypeptide comprising the predicted baboon TLR3 signal sequence and the extracellular domain.

Another aspect of the invention is an isolated polynucleotide comprising a polynucleotide having the sequence shown in SEQ ID NO: 3 or a complementary sequence thereof. The polynucleotide sequence shown in SEQ ID NO: 3 encodes a polypeptide comprising the predicted mature form of the baboon TLR3 extracellular domain, the transmembrane domain, and the cytoplasmic domain.

Another aspect of the invention is an isolated polynucleotide comprising a polynucleotide having the sequence shown in SEQ ID NO: 4 or a complementary sequence thereof. The polynucleotide sequence shown in SEQ ID NO: 4 encodes a polypeptide comprising the predicted baboon TLR3 signal peptide, the extracellular domain, the transmembrane domain, and the cytoplasmic domain.

The polynucleotides of the invention may be produced by chemical synthesis such as solid phase polynucleotide synthesis on an automated polynucleotide synthesizer. Alternatively, the polynucleotides of the invention may be produced by other techniques such a PCR based duplication, vector based duplication, or restriction enzyme based DNA manipulation techniques. Techniques for producing or obtaining polynucleotides of a given known sequence are well known in the art.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide (Gentz et al., Proc. Natl. Acad. Sci. (USA) 86:821-284, 1989) or the HA peptide tag (Wilson et al., Cell 37:767-778, 1984) which facilitate the purification of fused polypeptides.

Another embodiment of the invention is a vector comprising an isolated polynucleotide having a sequence shown in SEQ ID NO: 1, 2, 3, 4, 5 or 6. The polynucleotide sequence shown in SEQ ID NO: 5 comprises 5' and 3' sequences flanking an open reading frame encoding a peptide chain comprising full-length baboon TLR3. SEQ ID NO: 6 is a polynucleotide (DNA) expression vector designated p4668.

The vectors of the invention are useful for maintaining polynucleotides, duplicating polynucleotides, or driving expression of a polypeptide encoded by a vector of the invention in a biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picronaviruses and retroviruses and vectors derived from combinations thereof, such as cosmids and phagemids.

The vectors of the invention can be formulated in microparticles, with adjuvants, with lipid, buffer or other excipients as appropriate for a particular application. In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known in the art. An exemplary plasmid-derived expression vector useful for expression of the polypeptides of the invention comprises an E. coli origin of replication, an aph (3')-1a kanamycin resistance gene, HCMV immediate early promoter with intron A, a synthetic polyA sequence and a bovine growth hormone terminator. Another exemplary plasmid derived expression vector comprises an E. coli origin of replication, an ant(4')-1a kanamycin resistance gene, Rous sarcoma virus long terminal repeat sequences, HCMV immediate early promoter and an SV40 late polyA sequence.

Another embodiment of the invention is an isolated host cell comprising a vector of the invention. Representative host cell examples include Archaea cells; bacterial cells such as Streptococci, Staphylococci, Enterococci, E. coli, Streptomyces, cyanobacteria, B. subtilis and S. aureus; fungal cells such as Kluveromyces, Saccharomyces, Basidomycete, Candida albicans or Aspergillus; insect cells such as Drosophila S2 and Spodoptera Sf9; animal cells such as CHO, COS, HeLa, C127, 3T3, BHK, 293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be effected by methods well known to those skilled in the art (Davis et al., Basic Methods in Molecular Biology, 2$^{nd}$ ed., Appleton & Lange, Norwalk, Conn., 1994; Sambrook et al., Molecular Cloning: A Laboratory Manual, 3$^{rd}$ ed., Cold Spring Harbor Laboratory Press, Cold Spring Harbor, N.Y., 2001). These methods include calcium phosphate transfection, DEAE-Dextran mediated transfection, microinjection, cationic lipid-mediated transfection, electroporation, transduction, scrape loading, ballistic introduction and infection.

Another aspect of the invention is an isolated polypeptide comprising a polypeptide having the sequence shown in SEQ ID NO: 7. SEQ ID NO: 7 is a polypeptide comprising the predicted mature form of the baboon TLR3 extracellular domain.

Another aspect of the invention is an isolated polypeptide comprising a polypeptide having the sequence shown in SEQ ID NO: 8. SEQ ID NO: 8 is a polypeptide comprising the predicted baboon TLR3 signal peptide and the extracellular domain.

Another aspect of the invention is an isolated polypeptide comprising a polypeptide having the sequence shown in SEQ ID NO: 9. SEQ ID NO: 9 is a polypeptide comprising the predicted mature form of the baboon TLR3 extracellular domain, the transmembrane domain, and the cytoplasmic domain.

Another aspect of the invention is an isolated polypeptide comprising a polypeptide having the sequence shown in SEQ ID NO: 10. SEQ ID NO: 10 is a polypeptide comprising the predicted baboon TLR3 signal peptide, the extracellular domain, the transmembrane domain, and the cytoplasmic domain.

The polypeptides of the invention may be produced by chemical synthesis, such as solid phase peptide synthesis, on an automated peptide synthesizer. Alternatively, the polypeptides of the invention can be obtained from polynucleotides encoding these polypeptides by the use of cell-free expression systems such as reticulocyte lysate based expression systems, wheat germ extract based expression systems, and *Escherichia coli* extract based expression systems. The polypeptides of the invention can also be obtained by expression and isolation from cells harboring a nucleic acid sequence of the invention by techniques well known in the art, such as recombinant expression of easily isolated affinity labeled polypeptides. Those skilled in the art will recognize other techniques for obtaining the polypeptides of the invention.

The polypeptides of the invention may comprise fusion polypeptides comprising a polypeptide of the invention fused with second polypeptide. Such second polypeptides may be leader or secretory signal sequences, a pre- or pro- or preproprotein sequence, as well as naturally occurring, or partially synthetic sequences derived in part from a naturally occurring sequence or an entirely synthetic sequence. Secretory signal or leader polypeptide sequences may be selected to direct secretion of the polypeptides of the invention into the lumen of the endoplasmic reticulum or extracellular environment; such polypeptide sequences may be heterologous or endogenous to any polypeptide from a *Papio cynocephalus* monkey or comprise hybrids of these. Exemplary fusion proteins can be formed by conjugating together a baboon TLR3 polypeptide having an amino acid sequence shown in SEQ ID NO: 7, 8, 9, or 10, and an alternative scaffold such as designed ankyrin repeat protein (DARPins) (Stumpp and Amstutz, Curr. Opin. Durg Discov. Devel. 10:153-159, 2007), MIMETIBODY™ construct (Picha et al. Diabetes 57:1926-1934, 2008), other protein domains or peptides specific for other TLR3s, such as TLR7 or TLR9. Fusion proteins may generally be generated using either recombinant nucleic acid methods or by chemical synthesis methods well known in the art. A MIMETIBODY™ construct has the generic formula (I):

$$(Bp\text{-}Lk\text{-}(V2)_y\text{-}Hg\text{-}C_H2\text{-}C_H3)_{(t)}, \quad (I)$$

where Bp is a peptide or polypeptide capable of binding a molecule of interest, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region, y is 0 or 1, and t is independently an integer of 1 to 10.

It is possible to modify the structure of the polypeptides or fragments of the invention for such purposes as enhancing substrate specificity, stability, solubility, and the like. For example, a modified polypeptide can be produced in which the amino acid sequence has been altered, such as by amino acid substitution, deletion, or addition. It is contemplated that an isolated replacement of a leucine with an isoleucine or valine, an aspartate with a glutamate, a threonine with a serine, or a similar replacement of an amino acid with a structurally related amino acid (i.e., conservative mutations) will, in some instances but not all, not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The polypeptides of the invention can also be formulated in a pharmaceutically acceptable carrier or diluent. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions, such as pH adjusting and buffering agents. The concentration of the polypeptides of the invention in such pharmaceutical formulation can vary widely, i.e., from less than about 0.5%, usually at or at least about 1% to as much as 15 or 20% by weight and will be selected primarily based on fluid volumes, viscosities and other factors, according to the particular mode of administration selected.

The polypeptides and nucleic acids of the invention can also be provided in the form of a pharmaceutical preparation, such as a vaccine for eliciting an immune response, that can be provided in unit dose forms. The appropriate therapeutically effective dose can be determined readily by those of skill in the art. A determined dose may, if necessary, be repeated at appropriate time intervals selected as appropriate by a physician or other person skilled in the relevant art (e.g. nurse, veterinarian, or veterinary technician) during the treatment period.

The polypeptides of the invention can be lyophilized for storage and reconstituted in a suitable carrier prior to use. This technique has been shown to be effective with conventional protein preparations. Lyophilization and reconstitution techniques are well known in the art.

Another embodiment of the invention is a method for expressing a polypeptide comprising the steps of providing a host cell of the invention; culturing the host cell under conditions sufficient for the expression of at least one polypeptide comprising the sequence shown in SEQ ID NO: 7, SEQ ID NO: 8, SEQ ID NO: 9, SEQ ID NO: 10 or SEQ ID NO: 11; and optionally confirming expression of at least one polypeptide comprising the sequence shown in SEQ ID NO: 7, SEQ ID NO: 8, SEQ ID NO: 9, SEQ ID NO: 10 or SEQ ID NO: 11.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of a polypeptide can be confirmed using a variety of different techniques well known in the art. For example, expression of a polypeptide can be confirmed using detection reagents, such as antibodies or receptor ligands, specific for an expressed polypeptide. Antibodies that specifically bind to or cross-react with the baboon TLR3 polypeptides of the invention are one example of such reagents. TLR3 receptor ligands such as dsRNA or poly(I:C) that bind TLR3 are another example of such reagents. Detection reagents may be detectably labeled by conjugation or incorporation of a radiolabel, fluorophore, chromophore or other detectable molecule to, or into, the detection reagent. Expression of a polypeptide can also be confirmed by assaying for a biological activity associated with activation of TLR3s, such as activation of NF-κB or increased production of type I interferons. Assays may also utilize reporter gene constructs responsive to TLR3 activation. Reporter genes and reporter gene constructs useful for the assays include a reporter gene operatively linked to a promoter sensitive to NF-κB. Examples of such promoters include those for IL-6, IL-8 and IL-12 p40 (Murphy et al., Mol. Cell. Biol. 15:5258-5267, 1995; Libermann and Baltimore, Mol. Cell. Biol. 10:2327-2334, 1990; Mauviel et al., J. Immunol. 149:2969-2976, 1992). The reporter gene operatively linked to the TLR3-sensitive promoter can include, for example, luciferase, alkaline phosphatase, β-galactosidase, chloramphenicol acetyltransferase (CAT), or green-fluorescent protein (GFP). An exemplary TLR3 activity assay uses a reporter gene assay for TLR3 based on NF-κB activation induced by a poly(I:C) ligand. This assay has been established and is commonly used by practitioners in the field (Alexopoulos et al., Nature 413: 732-738, 2001; Häcker et al., EMBO J. 18:6973-6982, 1999).

Polypeptide expression can also be confirmed by identification of a polypeptide with the physical characteristics of a polypeptide of the invention in a preparation of polypeptides. For example, SDS-PAGE techniques and other well-known protein characterization techniques utilizing criteria such as, for example, protein molecular weight or isoelectric point can be used to confirm expression of the polypeptides of the invention. Protein purification techniques such as ammonium sulfate or ethanol precipitation, acid extraction, high-performance liquid chromatography, anion or cation exchange chromatography, phosphocellulose chromatography, hydrophobic interaction chromatography, affinity chromatography, hydroxyapatite chromatography and lectin chromatography can also be used to confirm expression of a polypeptide of the invention.

Importantly, in the methods of the invention the polypeptide expressed need not be isolated. Consequently, expression of a polypeptide may be confirmed to have occurred on, or in, a cell, or in a mixture of polypeptides for example. Flow cytometry based techniques such as fluorescence activated cell sorting (FACS) may also be used, when appropriate, to confirm expression of a polypeptide by a cell. As discussed above polypeptide expression may be confirmed using any suitable technique known in the art.

Another embodiment of the invention is a polypeptide produced by the methods of invention. Such polypeptides may comprise post-translational modifications including glycosylation or phosphorylation for example. Such polypeptides may also comprise alternative polypeptide forms such as splice variants, truncated forms, or proteolytically modified forms.

Another embodiment of the invention is an antibody that specifically binds a polypeptide of the invention. The polypeptides of the invention can be used to produce polyclonal or monoclonal antibodies against baboon TLR3. Techniques for making murine, chimeric, humanized and fully human monoclonal antibodies using protein or nucleic acid immunization are routine and well known to those skilled in the art. Additional discussion and description of such techniques can be found above.

Another embodiment of the invention is a method of determining cross-reactivity of a TLR3 modulator with *Papio cynocephalus* monkey TLR3. Even if the polypeptides and epitopes are preserved across species and in the species under consideration for a predictive model for a modulator, cross-reactivity of a modulator should be established before additional experimentation is performed (Loisel et al., Crit. Rev. in Onc. Hematol. 62:34-42, 2007). Cross-reactivity of modulators, antibodies of the invention and other TLR3 antibodies to polypeptides and other antigens may be assayed using for example competitive and non-competitive assay systems using techniques such as BIAcore analysis, FACS, analysis, immunofluorescence, immunocytochemistry, radioimmunoassays, ELISA, "sandwich" immunoassays, immunoprecipitation assays, western blots, immunoradiometric assays, fluorescent immunoassays, and protein A immunoassays. Such assays are routine and well known in the art (Ausubel et al., eds, 1994, Current Protocols in Molecular Biology, Vol. 1, John Wiley & Sons, Inc., New York). Cross-reactivity can also be evaluated by assaying for a biological activity associated with activation of TLR3. Additional discussion of such assays can be found above. For example, cross-reactivity of a human anti-TLR3 antibody modulator with baboon TLR3 polypeptide can be evaluated using assay assessing effect of the antibody on blocking activation of poly(I:C)-induced NF-κB activation downstream of TLR3.

Another embodiment of the invention is a method for determining if a TLR3 modulator is likely to be safe or unsafe for use in humans comprising providing a TLR3 modulator, a first *Papio cynocephalus* monkey, and a second *Papio cynocephalus* monkey; administering the TLR3 modulator to the first *Papio cynocephalus* monkey; and determining whether the first *Papio cynocephalus* monkey is presenting a deleterious symptom relative to the second monkey, where presentation of a deleterious symptom by the first *Papio cynocephalus* monkey shows the TLR3 modulator is potentially unsafe for use in humans and a lack of presentation of a deleterious symptom by the first *Papio cynocephalus* monkey shows the TLR3 therapeutic is potentially safe in humans.

In the methods of the invention the determination of whether the first *Papio cynocephalus* monkey is presenting a deleterious symptom relative to the second *Papio cynocephalus* monkey is readily accomplished. For example, a person of ordinary skill in the art such as a veterinarian, veterinarian's assistant, animal technician, or research scientist can determine if a symptom presented by an animal is deleterious. Examples of deleterious symptoms include death, coma, seizures, fever, organ failure, tissue abnormalities, impaired organ function, impaired tissue function, cancers, tumors, ulcers, bleeding, infections and the like. The TLR3 modulators that can be tested include an antibody, an antibody portion or fragment, a peptide, a polypeptide, an oligonucleotide, a small molecule, or a combination thereof.

The present invention will now be described with reference to the following specific, non-limiting examples.

Example 1

Isolation of Polynucleotides Encoding *Papio cynocephalus* TLR3 (Baboon TLR3)

*Papio cynocephalus* TLR3 cDNA was cloned from *Papio cynocephalus* tracheal primary epithelial cells. The baboon TLR3 cDNA encoded a protein of 905 amino acids and showed 95.7% identity and 96.9% similarity to the human TLR3 cDNA sequence shown in Seq ID NO: 13. *Papio cynocephalus* TLR3 protein had a predicted 23 amino acid signal sequence and the transmembrane domain was predicted to encompass amino acids 704-725.ss Tracheal epithelial cells were obtained by digesting tracheal rings from a normal *Papio cynocephalus* baboon. Tracheal bronchial epithelial cell isolation was performed essentially as described by Robinson and Wu (Robinson and Wu, J. Tissue Culture Methods 13:95-102, 1991). Cells were cultured and harvested for isolation of total RNA.

A 682 bp baboon TLR3 cDNA was successfully amplified by RT-PCR using human oligonucleotide primers 5'GATCTGTCTCATAATGGCTTGTCA 3' (SEQ ID NO: 14) and 5'GTTTATCAATCCTGTGAACATAT 3' (SEQ ID NO: 15). The resulting fragment was isolated and subcloned using the TOPO pCR4 kit (Invitrogen); plasmid DNA from transformants was isolated and sequenced. In order to clone the 5' end of the gene, RT-PCR was performed using human 5' and baboon 3' oligonucleotide primers 5' ATGAGACAGACTTTGCCTTGT 3' (SEQ ID NO: 16) and 5' CAAATGCTGTATATTATTATA 3' (SEQ ID NO: 17). To clone the 3' end of the gene, PCR was performed using baboon 5' and human 3' oligonucleotide primers (5' GTTAGAGTTATCATCGAAT 3' (SEQ ID NO: 18) and 5' TTAATGTACAGAGTTTTTGGA 3' (SEQ ID NO: 19). The resulting fragments were isolated, subcloned, and the plasmid DNA from transformants was isolated and sequenced.

Additionally, 5' and 3' baboon cDNA and untranslated regions (UTRs) were cloned by RT-PCR using primers derived from human 5' and 3' UTR sequences together with primers derived from obtained baboon TLR3 cDNA. The 5' region was cloned by RT-PCR using primers 5' CATCCAACAGAAT 3' (SEQ ID NO:20) and 5' CAAATGCTGTATATTATTATA 3' (SEQ ID NO:21). The 3' region was cloned by RT-PCR using primers 5' TTGAATATGCAGCATATATAA 3' (SEQ ID NO: 22) and 5' AACTTTTTAAATTGAGAAAGTT 3' (SEQ ID NO: 23). The resulting approximately 1,000 bp and 508 bp PCR fragments corresponding to 5' and 3' ends of the baboon TLR3 cDNA, respectively, were isolated and subcloned as described above. Plasmid DNA from transformants was isolated and sequenced. Full length baboon TLR3 cDNA sequence was obtained from sequences of the overlapping cloned baboon cDNA fragments. The full length baboon TLR3 polynucleotide sequence is shown in SEQ ID NO: 5. The predicted full length protein sequence is shown in SEQ ID NO: 10. The alignment between human and baboon TLR3 polypeptide sequences is shown in FIGS. 1A and 1B.

Example 2

Figure 3:
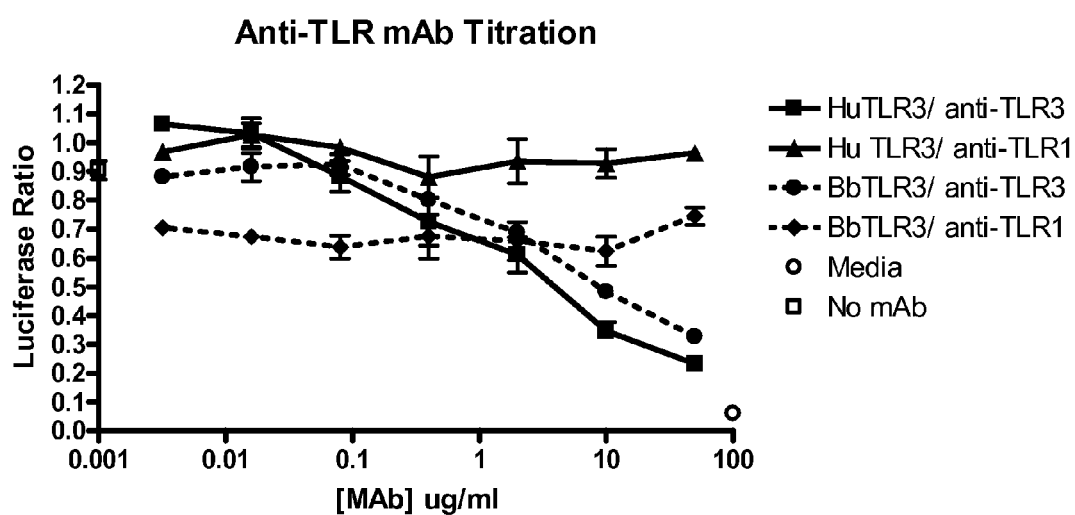
FIG. 3. Inhibition of poly(I:C)-induced NF-κB activation via *Papio cynocephalus* TLR3 by anti-human TLR3 antibody, but not by anti-human TLR1 antibody.

Baboon TLR3 cDNA Encodes a Functional Protein and Cross-Reacts with Anti-Human TLR3 Antibodies In order to assess functionality of the baboon TLR3, the ability of baboon TLR3 to activate downstream signaling pathways was assessed. Baboon TLR3 activated NF-κB upon induction with poly(I:C) in a similar manner when compared to the activation of NF-κB downstream of human TLR3 (FIG. 2). Furthermore, poly(I:C)-induced NF-κB activation was inhibited by an anti-human TLR3 polyclonal antibody. Anti-human TLR1 polyclonal antibody had no effect (FIG. 3).

The baboon TLR3 full length cDNA was cloned into the pBETH vector using oligonucleotide primers 5' ATTATTGCGGCCGCCACCATGAGACAGACTTTGCCTTGTATCTAC 3' (SEQ ID NO: 24) and 5' TAATAACTCGAGTTAATGTACAGAGTTTTTGGATCCAAGTG 3' (SEQ ID NO: 25) that included 5' NotI and 3' XhoI restriction sites, respectively. The resulting 2.7 kb PCR fragment was purified, digested with NotI and XhoI and subcloned into the corresponding sites of the expression vector pBETH (Invitrogen). sPlasmid DNA was purified and sequenced to confirm correct cloning of the baboon TLR3 cDNA. The construct was assigned the plasmid number p4668. 200 µL of HEK-293 cells were plated in each well of a 96 well white clear bottom plates at a concentration of 4×10⁴ cells/well in complete DMEM. After 24 hours, 70-90% confluent cells were transfected with plasmids containing firefly luciferase pNF-kB reporter plasmid (30 ng, Stratagene), phRL-TK control *Renilla* luciferase reporter plasmid (5 ng, Promega), plasmids containing human TLR3 or baboon TLR3 cDNA constructs (1.5 ng) and an empty pcDNA3.1 vector (13.5 ng, Invitrogen) to bring the total DNA amount to 50 ng/well using Lipofectamine 2000 (Invitrogen). Twenty-four hours after transfection, the cells were incubated for 1 hour at 37° C. with anti-human TLR3 (AF1487, R&D Systems) or anti-human TLR1 antibodies (AF1484, R&D Systems) in serum-free DMEM before the addition of 1 µg/mL poly(I:C) (GE-Amersham). After an additional incubation for 24 h, the cells were harvested using the Dual-Glo Luciferase Assay System reagents (Promega), and the relative light units were measured using a FLUOstar OPTIMA multi-detection reader with OPTIMA software (BMG Labtech GmbH, Germany).

The present invention now being fully described, it will be apparent to one of ordinary skill in the art that many changes and modifications can be made thereto without departing from the spirit or scope of the appended claims.

The invention claimed is:

1. An isolated polynucleotide encoding a polypeptide comprising the amino acid sequence shown in SEQ ID NO: 7.

2. The isolated polynucleotide of claim 1 having the sequence shown in SEQ ID NO: 1 or a complementary sequence thereof.

3. An isolated polynucleotide encoding a polypeptide comprising the amino acid sequence shown in SEQ ID NO: 8.

4. The isolated polynucleotide of claim 3 having the sequence shown in SEQ ID NO: 2 or a complementary sequence thereof.

5. An isolated polynucleotide encoding a polypeptide comprising the amino acid sequence shown in SEQ ID NO: 9.

6. The isolated polynucleotide of claim 5 having the sequence shown in SEQ ID NO: 3 or a complementary sequence thereof.

7. An isolated polynucleotide encoding a polypeptide comprising the amino acid sequence shown in SEQ ID NO: 10.

8. The isolated polynucleotide of claim 7 having the sequence shown in SEQ ID NO: 4 or a complementary sequence thereof.

9. A vector comprising an isolated polynucleotide having the sequence shown in SEQ ID NO: 1, 2, 3, or 4.

10. The vector of claim 9 that is an expression vector.

11. An isolated host cell comprising the vector of claim 9.

12. An isolated host cell comprising the vector of claim 10.

13. A method for expressing a polypeptide comprising the steps of:
   a. providing the host cell of claim 12; and
   b. culturing the host cell under conditions sufficient for the expression of at least one polypeptide comprising the sequence shown in SEQ ID NO: 7, SEQ ID NO: 8, SEQ ID NO: 9 or SEQ ID NO: 10.

* * * * *

```
                          SEQUENCE LISTING

<160> NUMBER OF SEQ ID NOS: 25

<210> SEQ ID NO 1
<211> LENGTH: 2040
<212> TYPE: DNA
<213> ORGANISM: Papio cynocepahlus

<400> SEQUENCE: 1
tccaccaaca aatgcactgt tagccaagaa gttgctgact gcagccacct gaagttaact      60
caggtacccg atgatctccc cacaaacata acagtgttga atcttaccca taatcaactc     120
aggagattac cagctgccaa ttttacaaga tatagccaac taactatctt ggatgtagga     180
tttaactcca tctcaaaact ggagccagaa ttgtgccaaa aacttcccat gttaaaagtt     240
ttgaacctcc agcacaatga gctatctcaa cttctgata aaacctttgc cttctgcacg      300
aatttgacgg aactccatct catgtccaac tcaatccaga aaattaaaag taatcccttt     360
gtaaagcaga agaatttaat cacattagat ctgtctcata atggcttgtc atctacaaaa     420
ttaggaactc aggttcagct ggaaaatctc caagagcttc tattatcaaa caataaaatc     480
caagcgctaa aaagtgaaga acttgatatc cttgccaatt catctttaaa aaagttagag     540
ttatcatcga atcaaattaa agagttttct ccagggtgtt ttcacgcaat tggaagatta     600 tgggcctct ttctgaacaa cgtccagctg ggtcccagcc tcacagagaa gctatgtttg      660
gaattagcaa acacaagcat tcggaatctg tctctgagta acagccagct gtccaccacc     720
agcaatacaa ctttcttggg actaaagtgg acaaacctca ctatgctcga tctttcccac     780
aacaacttaa atgtgattgg taacgattcc tttgtttggc ttccacatct agaatatttc     840
ttcctggagt ataataatat acagcatttg ctctctcact ctttgcacgg gcttttcaat     900
gtgcggtacc tgaatttgaa acggtctttt actaaacaaa gtatttccct tgcttcgctc     960
cccaagattg atgattttc tttcagtgg ctaacatgtt tggagcacct taacatggaa      1020
gataatgata tttcaggtat aaaaagcaat atgttcacag gattgataaa cctgaaatac     1080
ttaagtctat ccaactcctt tacaagtttg caaactttga caaatgaaac atttgtatca     1140
cttgctcatt ctcccttaca catactcaac ctaaccaaga ataaaatctc aaaaatagag     1200
agtggtgcct tctcttggtt gggccaccta gaagtacttg acctgggcct taatgaaatt     1260
gggcaagaac tcacaggcca ggaatggagt ggtctagaaa atattttcga aatctatctt     1320
tcctacaaca agtacctgca actgactaag aactcctttg ccttggtccg aagccttcaa     1380
cgactgatgc tccgaagggt ggcccttaaa aatgtggatt gctctccttc accattccag     1440
cctcttggta acctgaccat tctggatcta agcaacaaca acatagccaa cataaatgat     1500
gacatgttgg aaggtcttga gaaactagaa attctggatt tgcagcataa caacttagca     1560
cggctctgga aacacgcaaa ccctggtggt cctgtttatt tcctaaaagg tctgtctcac     1620
ctccacatcc ttaacttgga gtctaatggc tttgacgaga tcccagttga ggtcttcaag     1680
gatttatctg aactaaagat cattgattta ggattgaata atttaaacac acttccagag     1740
tctgtctttg ataatcaggt gtctctaaag tcattgaacc ttcagaagaa tctcataaca     1800
tcagttgaga agaaggtttt tgggccagct ttcaggaacc tgagtaactt agatatgcgc     1860
```

```
tttaatccct tgattgcac atgtgaaagt atcgcctggt tgttaactg gattaacaag    1920 acccatgcca acatccctga gctgtcaagc cactacctt  gcaacactcc acctcactat    1980
catgggttcc cagtgagact ttttgacaca tcatcctgca aagacagtgc cccctttgaa    2040
```

<210> SEQ ID NO 2
<211> LENGTH: 2109
<212> TYPE: DNA
<213> ORGANISM: Papio cynocephalus

<400> SEQUENCE: 2

```
atgagacaga ctttgcctta tatctacttt tggtggggac ttttgccctt tgggatgctg      60
tgtgcatcct ccaccaacaa atgcactgtt agccaagaag ttgctgactg cagccacctg     120
aagttaactc aggtacccga tgatctcccc acaaacataa cagtgttgaa tcttacccat     180
aatcaactca ggagattacc agctgccaat tttacaagat atagccaact aactatcttg     240
gatgtaggat ttaactccat ctcaaaactg gagccagaat tgtgccaaaa acttcccatg     300
ttaaaagttt tgaacctcca gcacaatgag ctatctcaac tttctgataa aacctttgcc     360
ttctgcacga atttgacgga actccatctc atgtccaact caatccagaa aattaaaagt     420 aatcccttg  taaagcagaa gaatttaatc acattagatc tgtctcataa tggcttgtca     480
tctacaaaat taggaactca ggttcagctg gaaaatctcc aagagcttct attatcaaac     540
aataaaatcc aagcgctaaa aagtgaagaa cttgatatcc ttgccaattc atctttaaaa     600
aagttagagt tatcatcgaa tcaaattaaa gagttttctc agggtgttt  tcacgcaatt     660 ggaagattat tgggcctctt tctgaacaac gtccagctgg gtcccagcct cacagagaag     720 ctatgttt gg aattagcaaa cacaagcatt cggaatctgt tctgagtaa  cagccagctg     780 tccaccacca gcaatacaac tttcttggga ctaaagtgga caaacctcac tatgctcgat     840 cttt cccaca caacttaaa  tgtgattggt aacgattcct ttgttt ggct tccacatcta     900 gaatatttct tcctggagta taataatata cagcatttgc tctctcactc tttgcacggg     960
cttttcaatg tgcggtacct gaatttgaaa cggtctttta ctaaacaaag tatttccctt    1020
gcttcgctcc ccaagattga tgatttttct tttcagtggc taacatgttt ggagcacctt    1080
aacatggaag ataatgatat ttcaggtata aaaagcaata tgttcacagg attgataaac    1140
ctgaaatact taagtctatc caactccttt acaagtttgc aaacttttgac aaatgaaaca    1200 tttgtatcac ttgctcattc tcccttacac atactcaacc taaccaagaa taaaatctca    1260
aaaatagaga gtggtgcctt ctcttggttg ggccacctag aagtacttga cctgggcctt    1320
aatgaaattg ggcaagaact cacaggccag gaatggagtg gtctagaaaa tatttt cgaa    1380 atctatcttt cctacaacaa gtacctgcaa ctgactaaga actcctttgc cttggtccga    1440
agccttcaac gactgatgct ccgaagggtg gcccttaaaa atgtggattg ctctccttca    1500
ccattccagc tcttggtaa  cctgaccatt ctggatctaa gcaacaacaa catagccaac    1560
ataaatgatg acatgttgga aggtcttgag aaactagaaa ttctggattt gcagcataac    1620
aacttagcac ggctctggaa acacgcaaac cctggtggtc ctgtttattt cctaaaaggt    1680
ctgtctcacc tccacatcct taacttggag tctaatggct ttgacgagat cccagttgag    1740
gtcttcaagg atttatctga actaaagatc attgatttag gattgaataa tttaaacaca    1800
cttccagagt ctgtctttga taatcaggtg tctctaaagt cattgaacct tcagaagaat    1860
ctcataacat cagttgagaa gaaggttttt gggccagctt tcaggaacct gagtaactta    1920
gatatgcgct ttaatccctt tgattgcaca tgtgaaagta tcgcctggtt tgttaactgg    1980
```

-continued

| | |
|---|---|
| attaacaaga cccatgccaa catccctgag ctgtcaagcc actacctttg caacactcca | 2040 |
| cctcactatc atgggttccc agtgagactt tttgacacat catcctgcaa agacagtgcc | 2100 |
| cccttttgaa | 2109 |

<210> SEQ ID NO 3
<211> LENGTH: 2646
<212> TYPE: DNA
<213> ORGANISM: Papio cynocephalus

<400> SEQUENCE: 3

| | |
|---|---|
| tccaccaaca aatgcactgt tagccaagaa gttgctgact gcagccacct gaagttaact | 60 |
| caggtacccg atgatctccc cacaaacata acagtgttga atcttaccca taatcaactc | 120 |
| aggagattac cagctgccaa ttttacaaga tatagccaac taactatctt ggatgtagga | 180 |
| tttaactcca tctcaaaact ggagccagaa ttgtgccaaa acttcccat gttaaaagtt | 240 |
| ttgaacctcc agcacaatga gctatctcaa cttttctgata aaacctttgc cttctgcacg | 300 |
| aatttgacgg aactccatct catgtccaac tcaatccaga aaattaaaag taatcccttt | 360 |
| gtaaagcaga agaatttaat cacattagat ctgtctcata atggcttgtc atctacaaaa | 420 |
| ttaggaactc aggttcagct ggaaaatctc caagagcttc tattatcaaa caataaaatc | 480 |
| caagcgctaa aaagtgaaga acttgatatc cttgccaatt catctttaaa aaagttagag | 540 |
| ttatcatcga atcaaattaa agagtttttct ccagggtgtt tcacgcaat tggaagatta | 600 |
| ttgggcctct ttctgaacaa cgtccagctg ggtcccagcc tcacagagaa gctatgtttg | 660 |
| gaattagcaa acacaagcat tcggaatctg tctctgagta cagccagct gtccaccacc | 720 |
| agcaatacaa cttttcttggg actaaagtgg acaaacctca ctatgctcga tcttttcccac | 780 |
| aacaacttaa atgtgattgg taacgattcc tttgtttggc ttccacatct agaatatttc | 840 |
| ttcctggagt ataataatat acagcatttg ctctctcact ctttgcacgg gcttttcaat | 900 |
| gtgcggtacc tgaatttgaa acggtctttt actaaacaaa gtatttccct tgcttcgctc | 960 |
| cccaagattg atgattttttc ttttcagtgg ctaacatgtt tggagcacct taacatggaa | 1020 |
| gataatgata tttcaggtat aaaaagcaat atgttcacag gattgataaa cctgaaatac | 1080 |
| ttaagtctat ccaactcctt tacaagtttg caaactttga caaatgaaac atttgtatca | 1140 |
| cttgctcatt ctcccttaca catactcaac ctaaccaaga ataaaatctc aaaaatagag | 1200 |
| agtggtgcct tctcttggtt gggccaccta gaagtacttg acctgggcct taatgaaatt | 1260 |
| gggcaagaac tcacaggcca ggaatggagt ggtctagaaa atattttcga aatctatctt | 1320 |
| tcctacaaca gtacctgca actgactaag aactccttg ccttggtccg aagccttcaa | 1380 |
| cgactgatgc tccgaagggt ggcccttaaa atgtgggatt gctctccttc accattccag | 1440 |
| cctcttggta acctgaccat tctggatcta agcaacaaca acatagccaa cataaatgat | 1500 |
| gacatgttgg aaggtcttga gaaactagaa attctggatt gcagcataa caacttagca | 1560 |
| cggctctgga acacgcaaa ccctggtggt cctgtttatt tcctaaaagg tctgtctcac | 1620 |
| ctccacatcc ttaacttgga gtctaatggc tttgacgaga tcccagttga ggtcttcaag | 1680 |
| gatttatctg aactaaagat cattgattta ggattgaata atttaaacac acttccagag | 1740 |
| tctgtctttg ataatcaggt gtctctaaag tcattgaacc ttcagaagaa tctcataaca | 1800 |
| tcagttgaga agaaggttttt tgggccagct ttcaggaacc tgagtaactt agatatgcgc | 1860 |
| tttaatccct tgattgcac atgtgaaagt atcgcctggt tgttaactg gattaacaag | 1920 |
| acccatgcca acatccctga gctgtcaagc cactaccttt gcaacactcc acctcactat | 1980 |

-continued

| | |
|---|---|
| catgggttcc cagtgagact tttgacaca tcatcctgca aagacagtgc ccccttgaa | 2040 |
| ctcctttca tgatcaatac cagtatcctg ttgatttta tctttgttgt acttctcatc | 2100 |
| cactttgagg gctggaggat atcttttac tggaatgttt cagtacatcg agttcttggt | 2160 |
| ttcagagaaa tagacagaca gacagaacag tttgaatatg cagcatatat aattcacgcc | 2220 |
| cataaagata aggattgggt ctgggaacat ttctcttcaa tggaaaagga agaccaatct | 2280 |
| ctcaaattt gtctggaaga aagggacttt gaggcaggtg ttttgaact ggaagcaatt | 2340 |
| gttaacagca tcaaaagaag cagaaaaatt atttttatta taacacacca tctattaaaa | 2400 |
| gacccattat gcaaaagatt caaggtacat catgccgttc aacaagctat tgaacaaaat | 2460 |
| ctggattcca ttatattgat tttccttgag gagattccag attataaact gaaccatgca | 2520 |
| ctctgtttga aagaggaat gtttaaatct cactgcatct tgaactggcc agttcagaaa | 2580 |
| gaacggatag gtgcctttca tcataaactg caagtagcac ttggatccaa aaactcagta | 2640 |
| cattaa | 2646 |

<210> SEQ ID NO 4
<211> LENGTH: 2715
<212> TYPE: DNA
<213> ORGANISM: Papio cynocephalus

<400> SEQUENCE: 4

| | |
|---|---|
| atgagacaga ctttgcctta tatctacttt tggtggggac ttttgcctt tgggatgctg | 60 |
| tgtgcatcct ccaccaacaa atgcactgtt agccaagaag ttgctgactg cagccacctg | 120 |
| aagttaactc aggtacccga tgatctcccc acaaacataa cagtgttgaa tcttacccat | 180 |
| aatcaactca ggagattacc agctgccaat tttacaagat atagccaact aactatcttg | 240 |
| gatgtaggat ttaactccat ctcaaaactg gagccagaat tgtgccaaaa acttcccatg | 300 |
| ttaaagtt tgaacctcca gcacaatgag ctatctcaac tttctgataa aacctttgcc | 360 |
| ttctgcacga atttgacgga actccatctc atgtccaact caatccagaa aattaaaagt | 420 |
| aatcccttg taaagcagaa gaatttaatc acattagatc tgtctcataa tggcttgtca | 480 |
| tctacaaaat taggaactca ggttcagctg gaaaatctcc aagagcttct attatcaaac | 540 |
| aataaaatcc aagcgctaaa aagtgaagaa cttgatatcc ttgccaattc atcttttaaaa | 600 |
| aagttagagt tatcatcgaa tcaaattaaa gagttttctc cagggtgttt tcacgcaatt | 660 |
| ggaagattat tgggcctctt tctgaacaac gtccagctgg gtcccagcct cacagagaag | 720 |
| ctatgtttgg aattagcaaa cacaagcatt cggaatctgt tctgagtaa cagccagctg | 780 |
| tccaccacca gcaatacaac tttcttggga ctaaagtgga caaacctcac tatgctcgat | 840 |
| ctttcccaca caaacttaaa tgtgattggt aacgattcct tgtttggct tccacatcta | 900 |
| gaatatttct tcctggagta taataatata cagcatttgc tctctcactc tttgcacggg | 960 |
| ctttttcaatg tgcggtacct gaatttgaaa cggtcttta ctaaacaaag tatttcccctt | 1020 |
| gcttcgctcc ccaagattga tgattttct tttcagtggc taacatgttt ggagcacctt | 1080 |
| aacatggaag ataatgatat ttcaggtata aaaagcaata tgttcacagg attgataaac | 1140 |
| ctgaaatact aagtctatc caactccttt acaagtttgc aaacttttgac aaatgaaaca | 1200 |
| tttgtatcac ttgctcattc tcccttacac atactcaacc taaccaagaa taaaatctca | 1260 |
| aaaatagaga gtggtgcctt ctcttggttg ggccacctag aagtacttga cctgggcctt | 1320 |
| aatgaaattg ggcaagaact cacaggccag gaatggagtg gtctagaaaa atttttcgaa | 1380 |
| atctatcttt cctacaacaa gtacctgcaa ctgactaaga actccttgc cttggtccga | 1440 |

```
agccttcaac gactgatgct ccgaagggtg gcccttaaaa atgtggattg ctctccttca   1500
ccattccagc ctcttggtaa cctgaccatt ctggatctaa gcaacaacaa catagccaac   1560
ataaatgatg acatgttgga aggtcttgag aaactagaaa ttctggattt gcagcataac   1620
aacttagcac ggctctggaa acacgcaaac cctggtggtc ctgtttattt cctaaaaggt   1680
ctgtctcacc tccacatcct taacttggag tctaatggct ttgacgagat cccagttgag   1740
gtcttcaagg atttatctga actaaagatc attgatttag gattgaataa tttaaacaca   1800
cttccagagt ctgtctttga taatcaggtg tctctaaagt cattgaacct tcagaagaat   1860
ctcataacat cagttgagaa gaaggttttt gggccagctt tcaggaacct gagtaactta   1920
gatatgcgct ttaatccctt tgattgcaca tgtgaaagta tcgcctggtt tgttaactgg   1980
attaacaaga cccatgccaa catccctgag ctgtcaagcc actacctttg caacactcca   2040
cctcactatc atgggttccc agtgagactt tttgacacat catcctgcaa agacagtgcc   2100
ccctttgaac tccttttcat gatcaatacc agtatcctgt tgatttttat ctttgttgta   2160
cttctcatcc actttgaggg ctggaggata tcttttttact ggaatgtttc agtacatcga   2220
gttcttggtt tcagagaaat agacagacag acagaacagt ttgaatatgc agcatatata   2280
attcacgccc ataaagataa ggattgggtc tgggaacatt tctcttcaat ggaaaaggaa   2340
gaccaatctc tcaaattttg tctggaagaa agggactttg aggcaggtgt ttttgaactg   2400
gaagcaattg ttaacagcat caaaagaagc agaaaaatta tttttattat aacacaccat   2460
ctattaaaag acccattatg caaaagattc aaggtacatc atgccgttca acaagctatt   2520
gaacaaaatc tggattccat tatattgatt ttccttgagg agattccaga ttataaactg   2580
aaccatgcac tctgtttgag aagaggaatg tttaaatctc actgcatctt gaactggcca   2640
gttcagaaag aacggatagg tgcctttcat cataaactgc aagtagcact tggatccaaa   2700
aactcagtac attaa                                                   2715
```

<210> SEQ ID NO 5
<211> LENGTH: 2733
<212> TYPE: DNA
<213> ORGANISM: Papio cynocephalus

<400> SEQUENCE: 5

```
gcggccgcca ccatgagaca gactttgcct tgtatctact tttggtgggg acttttgccc     60
tttgggatgc tgtgtgcatc ctccaccaac aaatgcactg ttagccaaga agttgctgac    120
tgcagccacc tgaagttaac tcaggtaccc gatgatctcc ccacaaacat aacagtgttg    180
aatcttaccc ataatcaact caggagatta ccagctgcca tttttacaag atatagccaa    240
ctaactatct tggatgtagg atttaactcc atctcaaaac tggagccaga attgtgccaa    300
aaacttccca tgttaaaagt tttgaacctc cagcacaatg agctatctca actttctgat    360
aaaacctttg ccttctgcac gaatttgacg gaactccatc tcatgtccaa ctcaatccag    420
aaaattaaaa gtaaccccct tgtaaagcag aagaatttaa tcacattaga tctgtctcat    480
aatggcttgt catctacaaa attaggaact caggttcagc tggaaaatct ccaagagctt    540
ctattatcaa acaataaaat ccaagcgcta aaaagtgaag aacttgatat ccttgccaat    600
tcatctttaa aaaagttaga gttatcatcg aatcaaatta aagagttttc tccagggtgt    660
tttcacgcaa ttggaagatt attgggcctc tttctgaaca acgtccagct gggtcccagc    720
ctcacagaga agctatgttt ggaattagca aacacaagca ttcggaatct gtctctgagt    780
aacagccagc tgtccaccac cagcaataca actttcttgg gactaaagtg gacaaacctc    840
```

```
actatgctcg atctttccca caacaactta aatgtgattg gtaacgattc ctttgtttgg      900
cttccacatc tagaatattt cttcctggag tataataata tacagcattt gctctctcac      960
tctttgcacg ggcttttcaa tgtgcggtac ctgaatttga aacggtcttt tactaaacaa     1020
agtatttccc ttgcttcgct ccccaagatt gatgattttt cttttcagtg ctaacatgt      1080
ttggagcacc ttaacatgga agataatgat atttcaggta taaaaagcaa tatgttcaca     1140
ggattgataa acctgaaata cttaagtcta tccaactcct ttacaagttt gcaaactttg     1200
acaaatgaaa catttgtatc acttgctcat tctcccttac acatactcaa cctaaccaag     1260
aataaaatct caaaaataga gagtggtgcc ttctcttggt tgggccacct agaagtactt     1320
gacctgggcc ttaatgaaat tgggcaagaa ctcacaggcc aggaatggag tggtctagaa     1380
aatattttcg aaatctatct ttcctacaac aagtacctgc aactgactaa gaactccttt     1440
gccttggtcc gaagccttca acgactgatg ctccgaaggg tggcccttaa aaatgtggat     1500
tgctctcctt caccattcca gcctcttggt aacctgacca ttctggatct aagcaacaac     1560
aacatagcca acataaatga tgacatgttg gaaggtcttg agaaactaga aattctggat     1620
ttgcagcata caacttagc acggctctgg aaacacgcaa accctggtgg tcctgtttat     1680
ttcctaaaag gtctgtctca cctccacatc cttaacttgg agtctaatgg ctttgacgag     1740
atcccagttg aggtcttcaa ggatttatct gaactaaaga tcattgattt aggattgaat     1800
aatttaaaca cacttccaga gtctgtcttt gataatcagg tgtctctaaa gtcattgaac     1860
cttcagaaga atctcataac atcagttgag aagaaggttt ttgggccagc tttcaggaac     1920
ctgagtaact tagatatgcg ctttaatccc tttgattgca catgtgaaag tatcgcctgg     1980
tttgttaact ggattaacaa gacccatgcc aacatccctg agctgtcaag ccactacctt     2040
tgcaacactc cacctcacta tcatgggttc ccagtgagac ttttttgacac atcatcctgc     2100
aaagacagtg cccccttgga actccttttc atgatcaata ccagtatcct gttgatttt     2160
atctttgttg tacttctcat ccactttgag ggctggagga tatctttta ctggaatgtt     2220
tcagtacatc gagttcttgg tttcagagaa atagacagac agacagaaca gtttgaatat     2280
gcagcatata taattcacgc ccataaagat aaggattggg tctgggaaca tttctcttca     2340
atggaaaagg aagaccaatc tctcaaattt tgtctggaag aaagggactt tgaggcaggt     2400
gttttttgaac tggaagcaat tgttaacagc atcaaaagaa gcagaaaat tattttatt     2460
ataacacacc atctattaaa agacccatta tgcaaaagat tcaaggtaca tcatgccgtt     2520
caacaagcta ttgaacaaaa tctggatccc attatattga ttttccttga ggagattcca     2580
gattataaac tgaaccatgc actctgtttg agaagaggaa tgtttaaatc tcactgcatc     2640
ttgaactggc cagttcagaa agaacggata ggtgccttct catcataact gcaagtagca     2700
cttggatcca aaactctgt acattaactc gag                                  2733
```

<210> SEQ ID NO 6
<211> LENGTH: 13867
<212> TYPE: DNA
<213> ORGANISM: Papio cynocephalus

<400> SEQUENCE: 6

```
gttgacattg attattgact agttattaat agtaatcaat tacggggtca ttagttcata       60
gcccatatat ggagttccgc gttacataac ttacggtaaa tggcccgcct ggctgaccgc      120
ccaacgaccc ccgcccattg acgtcaataa tgacgtatgt tcccatagta acgccaatag      180
ggactttcca ttgacgtcaa tgggtggagt atttacggta aactgcccac ttggcagtac      240
```

```
atcaagtgta tcatatgcca agtccgcccc ctattgacgt caatgacggt aaatggcccg    300
cctggcatta tgcccagtac atgaccttac gggactttcc tacttggcag tacatctacg    360
tattagtcat cgctattacc atggtgatgc ggttttggca gtacaccaat gggcgtggat    420
agcggtttga ctcacgggga tttccaagtc tccaccccat tgacgtcaat gggagtttgt    480
tttggcacca aaatcaacgg gactttccaa aatgtcgtaa taaccccgcc ccgttgacgc    540
aaatgggcgg taggcgtgta cggtgggagg tctatataag cagagctcgt ttagtgaacc    600
gtcagatcgc ctggagacgc catccacgct gttttgacct ccatagaaga caccgggacc    660
gatccagcct ccgcggccgg aacggtgca ttggaacgcg gattcccgt gccaagagtg     720 acgtaagtac cgcctataga gtctataggc ccacctcctt ggcttcttat gcatgctata    780
ctgtttttgg cttgggtct atacaccccc gcttcctcat gttataggtg atggtatagc    840
ttagcctata ggtgtgggtt attgaccatt attgaccact cccctattgg tgacgatact    900
ttccattact aatccataac atggctcttt gccacaactc tctttattgg ctatatgcca    960
atacactgtc cttcagagac tgacacggac tctgtatttt tacaggatgg ggtctcattt   1020
attatttaca aattcacata tacaacacca ccgtccccag tgcccgcagc ttttattaaa   1080
cataacgtgg gatctccacg cgaatctcgg gtacgtgttc cggacatggg ctcttctccg   1140
gtagcggcgg agcttctaca tccgagccct gctcccatgc ctccagcgac tcatggtcgc   1200
tcggcagctc cttgctccta acagtggagg ccagacttag gcacagcacg atgcccacca   1260
ccaccagtgt gccgcacaag gccgtggcgg tagggtatgt gtctgaaaat gagctcgggg   1320
agcgggcttg caccgctgac gcatttggaa gacttaaggc agcggcagaa gaagatgcag   1380
gcagctgagt tgttgtgttc tgataagagt cagaggtaac tcccgttgcg gtgctgttaa   1440
cggtggaggg cagtgtagtc tgagcagtac tcgttgctgc cgcgcgcgcc accagacata   1500
atagctgaca gactaacaga ctgttccttt ccatgggtct tttctgcagt caccgtcctt   1560
agatctgtct agaagctggg taccagctgc tagcaagctt gctagcggcc gccaccatga   1620
gacagctttt gccttgtatc tacttttggt ggggacttttt gcccttggg atgctgtgtg   1680 catcctccac caacaaatgc actgttagcc aagaagttgc tgactgcagc cacctgaagt   1740
taactcaggt acccgatgat ctccccacaa acataacagt gttgaatctt acccataatc   1800
aactcaggag attaccagct gccaatttta caagatatag ccaactaact atcttggatg   1860
taggatttaa ctccatctca aaactggagc cagaattgtg ccaaaaactt cccatgttaa   1920 aagtttgaa cctccagcac aatgagctat ctcaactttc tgataaaacc tttgccttct   1980
gcacgaattt gacggaactc catctcatgt ccaactcaat ccagaaaatt aaaagtaacc   2040
cctttgtaaa gcagaagaat ttaatcacat tagatctgtc tcataatggc ttgtcatcta   2100
caaaattagg aactcaggtt cagctggaaa atctccaaga gcttctatta tcaaacaata   2160
aaatccaagc gctaaaaagt gaagaacttg atatccttgc caattcatct ttaaaaaagt   2220
tagagttatc atcgaatcaa attaaagagt tttctccagg gtgttttcac gcaattggaa   2280
gattattggg cctctttctg aacaacgtcc agctgggtcc cagcctcaca gagaagctat   2340
gtttggaatt agcaaacaca agcattcgga atctgtctct gagtaacagc cagctgtcca   2400
ccaccagcaa tacaactttc ttgggactaa agtggacaaa cctcactatg ctcgatcttt   2460
cccacaacaa cttaaatgtg attggtaacg attcctttgt ttggcttcca catctagaat   2520
atttcttcct ggagtataat aatatacagc atttgctctc tcactctttg cacgggcttt   2580
tcaatgtgcg gtacctgaat ttgaaacggt cttttactaa acaaagtatt tcccttgctt   2640
```

```
cgctccccaa gattgatgat ttttcttttc agtggctaac atgtttggag caccttaaca    2700
tggaagataa tgatatttca ggtataaaaa gcaatatgtt cacaggattg ataaacctga    2760
aatacttaag tctatccaac tcctttacaa gtttgcaaac tttgacaaat gaaacatttg    2820
tatcacttgc tcattctccc ttacacatac tcacctaac caagaataaa atctcaaaaa    2880
tagagagtgg tgccttctct tggttgggcc acctagaagt acttgacctg ggccttaatg    2940
aaattgggca agaactcaca ggccaggaat ggagtggtct agaaaatatt ttcgaaatct    3000
atctttccta caacaagtac ctgcaactga ctaagaactc ctttgccttg gtccgaagcc    3060
ttcaacgact gatgctccga agggtggccc ttaaaaatgt ggattgctct ccttcaccat    3120
tccagcctct tggtaacctg accattctgg atctaagcaa caacaacata gccaacataa    3180
atgatgacat gttggaaggt cttgagaaac tagaaattct ggatttgcag cataacaact    3240
tagcacggct ctgaaacac gcaaaccctg gtggtcctgt ttatttccta aaaggtctgt    3300
ctcacctcca catccttaac ttggagtcta atggctttga cgagatccca gttgaggtct    3360
tcaaggattt atctgaacta agatcattg atttaggatt gaataattta aacacacttc    3420
cagagtctgt ctttgataat caggtgtctc taaagtcatt gaaccttcag aagaatctca    3480
taacatcagt tgagaagaag gttttttgggc cagctttcag gaacctgagt aacttagata    3540
tgcgctttaa tcccttgat tgcacatgtg aaagtatcgc ctggtttgtt aactggatta    3600
acaagaccca tgccaacatc cctgagctgt caagccacta cctttgcaac actccacctc    3660
actatcatgg gttcccagtg agacttttgt acacatcatc ctgcaaagac agtgcccccct    3720 ttgaactcct tttcatgatc aataccagta tcctgttgat ttttatcttt gttgtacttc    3780
tcatccactt tgagggctgg aggatatctt tttactggaa tgtttcagta catcgagttc    3840
ttggtttcag agaaatagac agacagacag aacagtttga atatgcagca tatataattc    3900
acgcccataa agataaggat tgggtctggg aacatttctc ttcaatggaa aggaagacc    3960 aatctctcaa attttgtctg gaagaaaggg acttgaggc aggtgttttt gaactggaag    4020
caattgttaa cagcatcaaa agaagcagaa aaattatttt tattataaca caccatctat    4080
taaaagaccc attatgcaaa agattcaagg tacatcatgc cgttcaacaa gctattgaac    4140
aaaatctgga tcccattata ttgattttcc ttgaggagat tccagattat aaactgaacc    4200
atgcactctg tttgagaaga ggaatgttta aatctcactg catcttgaac tggccagttc    4260
agaaagaacg gataggtgcc tttcatcata aactgcaagt agcacttgga tccaaaaact    4320
ctgtacatta actcgaggcc ggcaaggccg gatccagaca tgataagata cattgatgag    4380
tttggacaaa ccacaactag aatgcagtga aaaaaatgct ttatttgtga aatttgtgat    4440
gctattgctt tatttgtaac cattataagc tgcaataaac aagttaacaa caacaattgc    4500
attcatttta tgtttcaggt tcaggggag gtgtgggagg ttttttaaag caagtaaaac    4560
ctctacaaat gtggtatggc tgattatgat ccggctgcct cgcgcgtttc ggtgatgacg    4620
gtgaaaacct ctgacacatg cagctcccgg agacggtcac agcttgtctg taagcggatg    4680
ccgggagcag acaagcccgt caggcgtcag cgggtgttgg cgggtgtcgg ggcgcagcca    4740
tgaggtcgac tctagaggat cgatgccccg ccccggacga actaaacctg actacgacat    4800 ctctgccct tcttcgcggg gcagtgcatg taatcccttc agttggttgg tacaacttgc    4860
caactgggcc ctgttccaca tgtgacacgg gggggaccaa acacaaagg ggttctctga    4920 ctgtagttga catccttata aatgatgtg cacatttgcc aacactgagt ggctttcatc    4980
ctggagcaga ctttgcagtc tgtggactgc aacacaacat tgcctttatg tgtaactctt    5040
```

```
ggctgaagct cttacaccaa tgctggggga catgtacctc ccaggggccc aggaagacta    5100
cgggaggcta caccaacgtc aatcagaggg gcctgtgtag ctaccgataa gcggaccctc    5160
aagagggcat tagcaatagt gtttataagg cccccttgtt aaccctaaac gggtagcata    5220
tgcttcccgg gtagtagtat atactatcca gactaaccct aattcaatag catatgttac    5280
ccaacgggaa gcatatgcta tcgaattagg gttagtaaaa gggtcctaag gaacagcgat    5340
atctcccacc ccatgagctg tcacggtttt atttacatgg ggtcaggatt ccacgagggt    5400
agtgaaccat tttagtcaca agggcagtgg ctgaagatca aggagcgggc agtgaactct    5460
cctgaatctt cgcctgcttc ttcattctcc ttcgtttagc taatagaata actgctgagt    5520
tgtgaacagt aaggtgtatg tgaggtgctc gaaaacaagg tttcaggtga cgcccccaga    5580
ataaaatttg gacgggggt tcagtggtgg cattgtgcta tgacaccaat ataaccctca    5640 caaaccccctt gggcaataaa tactagtgta ggaatgaaac attctgaata tctttaacaa    5700
tagaaatcca tggggtgggg acaagccgta aagactggat gtccatctca cacgaattta    5760
tggctatggg caacacataa tcctagtgca atatgatact ggggttatta agatgtgtcc    5820
caggcaggga ccaagacagg tgaaccatgt tgttacactc tatttgtaac aaggggaaag    5880
agagtggacg ccgacagcag cggactccac tggttgtctc taacacccccc gaaaattaaa    5940 cggggctcca cgccaatggg gcccataaac aaagacaagt ggccactctt ttttttgaaa    6000
ttgtggagtg ggggcacgcg tcagccccca cacgccgccc tgcggttttg gactgtaaaa    6060
taagggtgta ataacttggc tgattgtaac cccgctaacc actgcggtca aaccacttgc    6120
ccacaaaacc actaatggca ccccggggaa tacctgcata agtaggtggg cgggccaaga    6180
taggggcgcg attgctgcga tctggaggac aaattacaca cacttgcgcc tgagcgccaa    6240
gcacagggtt gttggtcctc atattcacga ggtcgctgag agcacggtgg gctaatgttg    6300
ccatgggtag catatactac ccaaatatct ggatagcata tgctatccta atctatatct    6360
gggtagcata ggctatccta atctatatct gggtagcata tgctatccta atctatatct    6420
gggtagtata tgctatccta atttatatct gggtagcata ggctatccta atctatatct    6480
gggtagcata tgctatccta atctatatct gggtagtata tgctatccta atctgtatcc    6540
gggtagcata tgctatccta atagagatta gggtagtata tgctatccta atttatatct    6600
gggtagcata tactacccaa atatctggat agcatatgct atcctaatct atatctgggt    6660
agcatatgct atcctaatct atatctgggt agcataggct atcctaatct atatctgggt    6720
agcatatgct atcctaatct atatctgggt agtatatgct atcctaattt atatctgggt    6780
agcataggct atcctaatct atatctgggt agcatatgct atcctaatct atatctgggt    6840
agtatatgct atcctaatct gtatccgggt agcatatgct atcctcatgc atatacagtc    6900
agcatatgat acccagtagt agagtgggag tgctatcctt tgcatatgcc gccacctccc    6960
aagggggcgt gaattttcgc tgcttgtcct tttcctgctg gttgctccca ttcttaggtg    7020
aatttaagga ggccaggcta aagccgtcgc atgtctgatt gctcaccagg taaatgtcgc    7080
taatgttttc caacgcgaga aggtgttgag cgcggagctg agtgacgtga caacatgggt    7140
atgcccaatt gccccatgtt gggaggacga aaatggtgac aagacagatg ccagaaata     7200 caccaacagc acgcatgatg tctactgggg atttattctt tagtgcgggg gaatacacgg    7260 ctttttaatac gattgagggc gtctcctaac aagttacatc actcctgccc ttcctcaccc    7320
tcatctccat cacctccttc atctccgtca tctccgtcat caccctccgc ggcagcccct    7380
tccaccatag gtggaaacca gggaggcaaa tctactccat cgtcaaagct gcacacagtc    7440
```

-continued

```
accctgatat tgcaggtagg agcgggcttt gtcataacaa ggtccttaat cgcatccttc    7500
aaaacctcag caaatatatg agtttgtaaa aagaccatga aataacagac aatggactcc    7560
cttagcgggc caggttgtgg gccgggtcca ggggccattc caaaggggag acgactcaat    7620
ggtgtaagac gacattgtgg aatagcaagg gcagttcctc gccttaggtt gtaaagggag    7680
gtcttactac ctccatatac gaacacaccg gcgacccaag ttccttcgtc ggtagtcctt    7740
tctacgtgac tcctagccag gagagctctt aaaccttctg caatgttctc aaatttcggg    7800
ttggaacctc cttgaccacg atgcttttcc aaaccaccct cctttttgc gccctgcctc    7860 catcaccctg accccggggt ccagtgcttg ggccttctcc tgggtcatct gcggggccct    7920
gctctatcgc tcccgggggc acgtcaggct caccatctgg gccaccttct tggtggtatt    7980
caaaataatc ggcttcccct acagggtgga aaaatggcct tctacctgga gggggcctgc    8040
gcggtggaga cccggatgat gatgactgac tactgggact cctgggcctc ttttctccac    8100
gtccacgacc tctcccccctg gctctttcac gacttccccc cctggctctt tcacgtcctc    8160
taccccggcg gcctccacta cctcctcgac cccggcctcc actacctcct cgaccccggc    8220
ctccactgcc tcctcgaccc cggcctccac ctcctgctcc tgcccctcct gctcctgccc    8280
ctcctcctgc tcctgcccct cctgccccctc ctgctcctgc cctcctgcc cctcctgctc    8340 ctgcccctcc tgccctcct gctcctgccc ctcctgcccc tcctcctgct cctgcccctc    8400
ctgcccctcc tcctgctcct gcccctcctg ccctcctgc tcctgcccct cctgcccctc    8460
ctgctcctgc cctcctgcc cctcctgctc tgcccctcc tgctcctgcc cctcctgctc    8520
ctgcccctcc tgctcctgcc cctcctgccc ctcctgcct cctcctgct cctgcccctc    8580 ctgctcctgc cctcctgcc cctcctgctc tgcccctcct cctgctcctg    8640
cccctcctgc cctcctgcc cctcctcctg ctcctgcccc tcctgccct cctcctgctc    8700 ctgcccctcc tcctgctcct gcccctcctg ccctcctgc cctcctcct gctcctgccc    8760 ctcctgcccc tcctcctgct cctgcccctc ctcctgctc tgcccctcct gcccctcctg    8820
cccctcctcc tgctcctgcc cctcctgccc ctcctgccct cctgccct cctgcccctc    8880 ctgcccctcc tcctgctcct gccccctcctc ctgctcctgc cccctcctgct cctgcccctc    8940 ccgctcctgc tcctgctcct gttccaccgt gggtccctttt gcagccaatg caacttggac    9000 gttttttgggg tctccggaca ccatctctat gtcttggccc tgatcctgag ccgcccgggg    9060
ctcctggtct tccgcctcct cgtcctcgtc ctcttcccccg tcctcgtcca tggttatcac    9120
cccctcttct ttgaggtcca ctgccgccgg agccttctgg tccagatgtg tctcccttct    9180
ctcctaggcc attccaggt cctgtacctg gccccctcgtc agacatgatt cacactaaaa    9240
gagatcaata gacatctttta ttagacgacg ctcagtgaat acagggagtg cagactcctg    9300 cccctccaa cagcccccc accctcatcc ccttcatggt cgctgtcaga cagatccagg    9360
tctgaaaatt cccccatcctc cgaaccatcc tcgtcctcat caccaattac tcgcagcccg    9420
gaaaactccc gctgaacatc ctcaagattt gcgtcctgag cctcaagcca ggcctcaaat    9480
tcctcgtccc ccttttttgct ggacggtagg gatggggatt tcgggaccc ctcctcttcc    9540 tcttcaaggt caccagacag agatgctact ggggcaacgg aagaaaagct gggtgcggcc    9600
tgtgaggatc agcttatcga tgataagctg tcaaacatga gaattcttga agacgaaagg    9660
gcctcgtgat acgcctattt ttataggtta atgtcatgat aataatggtt tcttagacgt    9720
caggtggcac ttttcgggga aatgtgcgcg gaaccctat ttgtttattt ttctaaatac    9780
attcaaatat gtatccgctc atgagacaat aaccctgata aatgcttcaa taatattgaa    9840
```

-continued

```
aaaggaagag tatgagtatt caacatttcc gtgtcgccct tattcccttt tttgcggcat    9900
tttgccttcc tgttttgct cacccagaaa cgctggtgaa agtaaaagat gctgaagatc    9960
agttgggtgc acgagtgggt tacatcgaac tggatctcaa cagcggtaag atccttgaga   10020
gttttcgccc cgaagaacgt tttccaatga tgagcacttt taaagttctg ctatgtggcg   10080
cggtattatc ccgtgttgac gccgggcaag agcaactcgg tcgccgcata cactattctc   10140
agaatgactt ggttgagtac tcaccagtca cagaaaagca tcttacggat ggcatgacag   10200
taagagaatt atgcagtgct gccataacca tgagtgataa cactgcggcc aacttacttc   10260
tgacaacgat cggaggaccg aaggagctaa ccgcttttt gcacaacatg ggggatcatg   10320
taactcgcct tgatcgttgg gaaccggagc tgaatgaagc cataccaaac gacgagcgtg   10380
acaccacgat gcctgcagca atggcaacaa cgttgcgcaa actattaact ggcgaactac   10440
ttactctagc ttcccggcaa caattaatag actggatgga ggcggataaa gttgcaggac   10500
cacttctgcg ctcggccctt ccggctggct ggtttattgc tgataaatct ggagccggtg   10560
agcgtgggtc tcgcggtatc attgcagcac tggggccaga tggtaagccc tcccgtatcg   10620
tagttatcta cacgacgggg agtcaggcaa ctatggatga acgaaataga cagatcgctg   10680
agataggtgc ctcactgatt aagcattggt aactgtcaga ccaagtttac tcatatatac   10740
tttagattga tttaaaactt cattttaat ttaaaaggat ctaggtgaag atcctttttg   10800
ataatctcat gaccaaaatc ccttaacgtg agttttcgtt ccactgagcg tcagaccccg   10860
tagaaaagat caaaggatct tcttgagatc ctttttttct gcgcgtaatc tgctgcttgc   10920
aaacaaaaaa accaccgcta ccagcggtgg tttgtttgcc ggatcaagag ctaccaactc   10980
tttttccgaa ggtaactggc ttcagcagag cgcagatacc aaatactgtc cttctagtgt   11040
agccgtagtt aggccaccac ttcaagaact ctgtagcacc gcctacatac ctcgctctgc   11100
taatcctgtt accagtggct gctgccagtg gcgataagtc gtgtcttacc gggttggact   11160
caagacgata gttaccggat aaggcgcagc ggtcgggctg aacggggggt tcgtgcacac   11220
agcccagctt ggagcgaacg acctacaccg aactgagata cctacagcgt gagctatgag   11280
aaagcgccac gcttcccgaa gggagaaagg cggacaggta tccggtaagc ggcagggtcg   11340
gaacaggaga gcgcacgagg gagcttccag ggggaaacgc ctggtatctt tatagtcctg   11400
tcgggtttcg ccacctctga cttgagcgtc gatttttgtg atgctcgtca gggggggcgga   11460 gcctatggaa aaacgccagc aacgcggcct ttttacggtt cctggccttt tgctggcctt   11520
gaagctgtcc ctgatggtcg tcatctacct gcctggacag catggcctgc aacgcgggca   11580
tcccgatgcc gccggaagcg agaagaatca taatgggaa ggccatccag cctcgcgtcg   11640
cgaacgccag caagacgtag cccagcgcgt cggccccgag atgcgccgcg tgcggctgct   11700
ggagatggcg gacgcgatgg atatgttctg ccaaggggttg gtttgcgcat tcacagttct   11760
ccgcaagaat tgattggctc caattcttgg agtggtgaat ccgttagcga ggtgccgccc   11820
tgcttcatcc ccgtggcccg ttgctcgcgt ttgctggcgg tgtccccgga agaaatatat   11880
ttgcatgtct ttagttctat gatgacacaa accccgccca gcgtcttgtc attggcgaat   11940
tcgaacacgc agatgcagtc ggggcggcgc ggtccgaggt ccacttcgca tattaaggtg   12000
acgcgtgtgg cctcgaacac cgagcgaccc tgcagcgacc cgcttaacag cgtcaacagc   12060
gtgccgcaga tcccggggg caatgagata tgaaaaagcc tgaactcacc gcgacgtctg   12120
tcgagaagtt tctgatcgaa aagttcgaca gcgtctccga cctgatgcag ctctcggagg   12180
gcgaagaatc tcgtgctttc agcttcgatg taggagggcg tggatatgtc ctgcgggtaa   12240
```

-continued

```
atagctgcgc cgatggtttc tacaaagatc gttatgttta tcggcacttt gcatcggccg   12300
cgctcccgat tccggaagtg cttgacattg gggaattcag cgagagcctg acctattgca   12360
tctcccgccg tgcacagggt gtcacgttgc aagacctgcc tgaaaccgaa ctgcccgctg   12420
ttctgcagcc ggtcgcggag gccatggatg cgatcgctgc ggccgatctt agccagacga   12480
gcgggttcgg cccattcgga ccgcaaggaa tcggtcaata cactacatgg cgtgatttca   12540
tatgcgcgat gctgatcccc atgtgtatc actggcaaac tgtgatggac gacaccgtca   12600
gtgcgtccgt cgcgcaggct ctcgatgagc tgatgctttg gccgaggac tgccccgaag    12660 tccggcacct cgtgcacgcg gatttcggct ccaacaatgt cctgacggac aatggccgca   12720
taacagcggt cattgactgg agcgaggcga tgttcgggga ttcccaatac gaggtcgcca   12780
acatcttctt ctggaggccg tggttggctt gtatggagca gcagacgcgc tacttcgagc   12840
ggaggcatcc ggagcttgca ggatcgccgc ggctccgggc gtatatgctc cgcattggtc   12900
ttgaccaact ctatcagagc ttggttgacg gcaatttcga tgatgcagct tgggcgcagg   12960
gtcgatgcga cgcaatcgtc cgatccggag ccgggactgt cgggcgtaca caaatcgccc   13020
gcagaagcgc ggccgtctgg accgatggct gtgtagaagt actcgccgat agtgaaaacc   13080 gacgcccag cactcgtccg gatcgggaga tgggggaggc taactgaaac acggaaggag    13140
acaataccgg aaggaacccg cgctatgacg gcaataaaaa gacagaataa acgcacgggg   13200
tgttgggtcg tttgttcata aacgcggggt tcggtcccag ggctggcact ctgtcgatac   13260
cccaccgaga ccccattggg gccaatacgc ccgcgtttct tcctttcccc caccccaccc   13320
cccaagttcg ggtgaaggcc cagggctcgc agccaacgtc ggggcggcag gccctgccat   13380
agccactggc cccgtgggtt agggacgggg tcccccatgg ggaatggttt atggttcgtg   13440
ggggttatta ttttgggcgt tgcgtgggt caggtccacg actggactga gcagacagac    13500
ccatggtttt tggatggcct gggcatggac cgcatgtact ggcgcgacac gaacaccggg   13560
cgtctgtggc tgccaaacac ccccgacccc caaaaaccac cgcgcggatt tctggcgtgc   13620
caagctagtc gaccaattct catgtttgac agcttatcat cgcagatccg gcaacgttg    13680 ttgccattgc tgcaggcgca gaactggtag gtatggaaga tctatacatt gaatcaatat   13740
tggcaattag ccatattagt cattggttat atagcataaa tcaatattgg ctattggcca   13800
ttgcatacgt tgtatctata tcataatatg tacatttata ttggctcatg tccaatatga   13860
ccgccat                                                            13867
```

<210> SEQ ID NO 7
<211> LENGTH: 680
<212> TYPE: PRT
<213> ORGANISM: Papio cynocephalus

<400> SEQUENCE: 7

```
Ser Thr Asn Lys Cys Thr Val Ser Gln Glu Val Ala Asp Cys Ser His
 1               5                  10                  15

Leu Lys Leu Thr Gln Val Pro Asp Asp Leu Pro Thr Asn Ile Thr Val
            20                  25                  30

Leu Asn Leu Thr His Asn Gln Leu Arg Arg Leu Pro Ala Ala Asn Phe
        35                  40                  45

Thr Arg Tyr Ser Gln Leu Thr Ile Leu Asp Val Gly Phe Asn Ser Ile
    50                  55                  60

Ser Lys Leu Glu Pro Glu Leu Cys Gln Lys Leu Pro Met Leu Lys Val
65                  70                  75                  80

Leu Asn Leu Gln His Asn Glu Leu Ser Gln Leu Ser Asp Lys Thr Phe
```

```
                85                  90                  95
Ala Phe Cys Thr Asn Leu Thr Glu Leu His Leu Met Ser Asn Ser Ile
            100                 105                 110

Gln Lys Ile Lys Ser Asn Pro Phe Val Lys Gln Lys Asn Leu Ile Thr
            115                 120                 125

Leu Asp Leu Ser His Asn Gly Leu Ser Ser Thr Lys Leu Gly Thr Gln
            130                 135                 140

Val Gln Leu Glu Asn Leu Gln Glu Leu Leu Leu Ser Asn Asn Lys Ile
145                 150                 155                 160

Gln Ala Leu Lys Ser Glu Glu Leu Asp Ile Leu Ala Asn Ser Ser Leu
                165                 170                 175

Lys Lys Leu Glu Leu Ser Ser Asn Gln Ile Lys Glu Phe Ser Pro Gly
            180                 185                 190

Cys Phe His Ala Ile Gly Arg Leu Phe Gly Leu Phe Leu Asn Asn Val
            195                 200                 205

Gln Leu Gly Pro Ser Leu Thr Glu Lys Leu Cys Leu Glu Leu Ala Asn
            210                 215                 220

Thr Ser Ile Arg Asn Leu Ser Leu Ser Asn Ser Gln Leu Ser Thr Thr
225                 230                 235                 240

Ser Asn Thr Thr Phe Leu Gly Leu Lys Trp Thr Asn Leu Thr Met Leu
                245                 250                 255

Asp Leu Ser His Asn Asn Leu Asn Val Ile Gly Asn Asp Ser Phe Val
            260                 265                 270

Trp Leu Pro His Leu Glu Tyr Phe Phe Leu Glu Tyr Asn Asn Ile Gln
            275                 280                 285

His Leu Leu Ser His Ser Leu His Gly Leu Phe Asn Val Arg Tyr Leu
            290                 295                 300

Asn Leu Lys Arg Ser Phe Thr Lys Gln Ser Ile Ser Leu Ala Ser Leu
305                 310                 315                 320

Pro Lys Ile Asp Asp Phe Ser Phe Gln Trp Leu Thr Cys Leu Glu His
                325                 330                 335

Leu Asn Met Glu Asp Asn Asp Ile Ser Gly Ile Lys Ser Asn Met Phe
            340                 345                 350

Thr Gly Leu Ile Asn Leu Lys Tyr Leu Ser Leu Ser Asn Ser Phe Thr
            355                 360                 365

Ser Leu Gln Thr Leu Thr Asn Glu Thr Phe Val Ser Leu Ala His Ser
            370                 375                 380

Pro Leu His Ile Leu Asn Leu Thr Lys Asn Lys Ile Ser Lys Ile Glu
385                 390                 395                 400

Ser Gly Ala Phe Ser Trp Leu Gly His Leu Glu Val Leu Asp Leu Gly
                405                 410                 415

Leu Asn Glu Ile Gly Gln Glu Leu Thr Gly Gln Glu Trp Ser Gly Leu
            420                 425                 430

Glu Asn Ile Phe Glu Ile Tyr Leu Ser Tyr Asn Lys Tyr Leu Gln Leu
            435                 440                 445

Thr Lys Asn Ser Phe Ala Leu Val Arg Ser Leu Gln Arg Leu Met Leu
            450                 455                 460

Arg Arg Val Ala Leu Lys Asn Val Asp Cys Ser Pro Ser Pro Phe Gln
465                 470                 475                 480

Pro Leu Gly Asn Leu Thr Ile Leu Asp Leu Ser Asn Asn Asn Ile Ala
                485                 490                 495

Asn Ile Asn Asp Asp Met Leu Glu Gly Leu Glu Lys Leu Glu Ile Leu
            500                 505                 510
```

```
Asp Leu Gln His Asn Asn Leu Ala Arg Leu Trp Lys His Ala Asn Pro
        515                 520                 525

Gly Gly Pro Val Tyr Phe Leu Lys Gly Leu Ser Leu His Ile Leu
        530                 535                 540

Asn Leu Glu Ser Asn Gly Phe Asp Glu Ile Pro Val Glu Val Phe Lys
545                 550                 555                 560

Asp Leu Ser Glu Leu Lys Ile Ile Asp Leu Gly Leu Asn Asn Leu Asn
                565                 570                 575

Thr Leu Pro Glu Ser Val Phe Asp Asn Gln Val Ser Leu Lys Ser Leu
            580                 585                 590

Asn Leu Gln Lys Asn Leu Ile Thr Ser Val Glu Lys Lys Val Phe Gly
        595                 600                 605

Pro Ala Phe Arg Asn Leu Ser Asn Leu Asp Met Arg Phe Asn Pro Phe
        610                 615                 620

Asp Cys Thr Cys Glu Ser Ile Ala Trp Phe Val Asn Trp Ile Asn Lys
625                 630                 635                 640

Thr His Ala Asn Ile Pro Glu Leu Ser Ser His Tyr Leu Cys Asn Thr
                645                 650                 655

Pro Pro His Tyr His Gly Phe Pro Val Arg Leu Phe Asp Thr Ser Ser
            660                 665                 670

Cys Lys Asp Ser Ala Pro Phe Glu
        675                 680

<210> SEQ ID NO 8
<211> LENGTH: 703
<212> TYPE: PRT
<213> ORGANISM: Papio cynocephalus

<400> SEQUENCE: 8

Met Arg Gln Thr Leu Pro Tyr Ile Tyr Phe Trp Trp Gly Leu Leu Pro
1               5                   10                  15

Phe Gly Met Leu Cys Ala Ser Ser Thr Asn Lys Cys Thr Val Ser Gln
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ile Leu
65                  70                  75                  80

Asp Val Gly Phe Asn Ser Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Ser Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Leu Ala Asn Ser Ser Leu Lys Lys Leu Glu Leu Ser Ser Asn Gln
        195                 200                 205
```

-continued

```
Ile Lys Glu Phe Ser Pro Gly Cys Phe His Ala Ile Gly Arg Leu Leu
210                 215                 220
Gly Leu Phe Leu Asn Asn Val Gln Leu Gly Pro Ser Leu Thr Glu Lys
225                 230                 235                 240
Leu Cys Leu Glu Leu Ala Asn Thr Ser Ile Arg Asn Leu Ser Leu Ser
                245                 250                 255
Asn Ser Gln Leu Ser Thr Thr Ser Asn Thr Thr Phe Leu Gly Leu Lys
            260                 265                 270
Trp Thr Asn Leu Thr Met Leu Asp Leu Ser His Asn Asn Leu Asn Val
        275                 280                 285
Ile Gly Asn Asp Ser Phe Val Trp Leu Pro His Leu Glu Tyr Phe Phe
290                 295                 300
Leu Glu Tyr Asn Asn Ile Gln His Leu Ser His Ser Leu His Gly
305                 310                 315                 320
Leu Phe Asn Val Arg Tyr Leu Asn Leu Lys Arg Ser Phe Thr Lys Gln
                325                 330                 335
Ser Ile Ser Leu Ala Ser Leu Pro Lys Ile Asp Asp Phe Ser Phe Gln
            340                 345                 350
Trp Leu Thr Cys Leu Glu His Leu Asn Met Glu Asp Asn Asp Ile Ser
        355                 360                 365
Gly Ile Lys Ser Asn Met Phe Thr Gly Leu Ile Asn Leu Lys Tyr Leu
370                 375                 380
Ser Leu Ser Asn Ser Phe Thr Ser Leu Gln Thr Leu Thr Asn Glu Thr
385                 390                 395                 400
Phe Val Ser Leu Ala His Ser Pro Leu His Ile Leu Asn Leu Thr Lys
                405                 410                 415
Asn Lys Ile Ser Lys Ile Glu Ser Gly Ala Phe Ser Trp Leu Gly His
            420                 425                 430
Leu Glu Val Leu Asp Leu Gly Leu Asn Glu Ile Gly Gln Glu Leu Thr
        435                 440                 445
Gly Gln Glu Trp Ser Gly Leu Glu Asn Ile Phe Glu Ile Tyr Leu Ser
450                 455                 460
Tyr Asn Lys Tyr Leu Gln Leu Thr Lys Asn Ser Phe Ala Leu Val Arg
465                 470                 475                 480
Ser Leu Gln Arg Leu Met Leu Arg Arg Val Ala Leu Lys Asn Val Asp
                485                 490                 495
Cys Ser Pro Ser Pro Phe Gln Pro Leu Gly Asn Leu Thr Ile Leu Asp
            500                 505                 510
Leu Ser Asn Asn Asn Ile Ala Asn Ile Asn Asp Asp Met Leu Glu Gly
        515                 520                 525
Leu Glu Lys Leu Glu Ile Leu Asp Leu Gln His Asn Asn Leu Ala Arg
530                 535                 540
Leu Trp Lys His Ala Asn Pro Gly Gly Pro Val Tyr Phe Leu Lys Gly
545                 550                 555                 560
Leu Ser His Leu His Ile Leu Asn Leu Glu Ser Asn Gly Phe Asp Glu
                565                 570                 575
Ile Pro Val Glu Val Phe Lys Asp Leu Ser Glu Leu Lys Ile Ile Asp
            580                 585                 590
Leu Gly Leu Asn Asn Leu Asn Thr Leu Pro Glu Ser Val Phe Asp Asn
        595                 600                 605
Gln Val Ser Leu Lys Ser Leu Asn Leu Gln Lys Asn Leu Ile Thr Ser
610                 615                 620
Val Glu Lys Lys Val Phe Gly Pro Ala Phe Arg Asn Leu Ser Asn Leu
625                 630                 635                 640
```

```
Asp Met Arg Phe Asn Pro Phe Asp Cys Thr Cys Glu Ser Ile Ala Trp
            645                 650                 655
Phe Val Asn Trp Ile Asn Lys Thr His Ala Asn Ile Pro Glu Leu Ser
            660                 665                 670
Ser His Tyr Leu Cys Asn Thr Pro Pro His Tyr His Gly Phe Pro Val
            675                 680                 685
Arg Leu Phe Asp Thr Ser Ser Cys Lys Asp Ser Ala Pro Phe Glu
            690                 695                 700

<210> SEQ ID NO 9
<211> LENGTH: 881
<212> TYPE: PRT
<213> ORGANISM: Papio cynocephalus

<400> SEQUENCE: 9

Ser Thr Asn Lys Cys Thr Val Ser Gln Glu Val Ala Asp Cys Ser His
  1               5                  10                  15
Leu Lys Leu Thr Gln Val Pro Asp Asp Leu Pro Thr Asn Ile Thr Val
             20                  25                  30
Leu Asn Leu Thr His Asn Gln Leu Arg Arg Leu Pro Ala Ala Asn Phe
         35                  40                  45
Thr Arg Tyr Ser Gln Leu Thr Ile Leu Asp Val Gly Phe Asn Ser Ile
     50                  55                  60
Ser Lys Leu Glu Pro Glu Leu Cys Gln Lys Leu Pro Met Leu Lys Val
 65                  70                  75                  80
Leu Asn Leu Gln His Asn Glu Leu Ser Gln Leu Ser Asp Lys Thr Phe
                 85                  90                  95
Ala Phe Cys Thr Asn Leu Thr Glu Leu His Leu Met Ser Asn Ser Ile
            100                 105                 110
Gln Lys Ile Lys Ser Asn Pro Phe Val Lys Gln Lys Asn Leu Ile Thr
        115                 120                 125
Leu Asp Leu Ser His Asn Gly Leu Ser Ser Thr Lys Leu Gly Thr Gln
    130                 135                 140
Val Gln Leu Glu Asn Leu Gln Glu Leu Leu Leu Ser Asn Asn Lys Ile
145                 150                 155                 160
Gln Ala Leu Lys Ser Glu Glu Leu Asp Ile Leu Ala Asn Ser Ser Leu
                165                 170                 175
Lys Lys Leu Glu Leu Ser Ser Asn Gln Ile Lys Glu Phe Ser Pro Gly
            180                 185                 190
Cys Phe His Ala Ile Gly Arg Leu Leu Gly Leu Phe Leu Asn Asn Val
        195                 200                 205
Gln Leu Gly Pro Ser Leu Thr Glu Lys Leu Cys Leu Glu Leu Ala Asn
    210                 215                 220
Thr Ser Ile Arg Asn Leu Ser Leu Ser Asn Ser Gln Leu Ser Thr Thr
225                 230                 235                 240
Ser Asn Thr Thr Phe Leu Gly Leu Lys Trp Thr Asn Leu Thr Met Leu
                245                 250                 255
Asp Leu Ser His Asn Asn Leu Asn Val Ile Gly Asn Asp Ser Phe Val
            260                 265                 270
Trp Leu Pro His Leu Glu Tyr Phe Phe Leu Glu Tyr Asn Asn Ile Gln
        275                 280                 285
His Leu Leu Ser His Ser Leu His Gly Leu Phe Asn Val Arg Tyr Leu
    290                 295                 300
Asn Leu Lys Arg Ser Phe Thr Lys Gln Ser Ile Ser Leu Ala Ser Leu
305                 310                 315                 320
```

```
Pro Lys Ile Asp Asp Phe Ser Phe Gln Trp Leu Thr Cys Leu Glu His
            325                 330                 335
Leu Asn Met Glu Asp Asn Asp Ile Ser Gly Ile Lys Ser Asn Met Phe
            340                 345                 350
Thr Gly Leu Ile Asn Leu Lys Tyr Leu Ser Leu Ser Asn Ser Phe Thr
            355                 360                 365
Ser Leu Gln Thr Leu Thr Asn Glu Thr Phe Val Ser Leu Ala His Ser
370                 375                 380
Pro Leu His Ile Leu Asn Leu Thr Lys Asn Lys Ile Ser Lys Ile Glu
385                 390                 395                 400
Ser Gly Ala Phe Ser Trp Leu Gly His Leu Glu Val Leu Asp Leu Gly
            405                 410                 415
Leu Asn Glu Ile Gly Gln Glu Leu Thr Gly Gln Glu Trp Ser Gly Leu
            420                 425                 430
Glu Asn Ile Phe Glu Ile Tyr Leu Ser Tyr Asn Lys Tyr Leu Gln Leu
            435                 440                 445
Thr Lys Asn Ser Phe Ala Leu Val Arg Ser Leu Gln Arg Leu Met Leu
    450                 455                 460
Arg Arg Val Ala Leu Lys Asn Val Asp Cys Ser Pro Ser Pro Phe Gln
465                 470                 475                 480
Pro Leu Gly Asn Leu Thr Ile Leu Asp Leu Ser Asn Asn Asn Ile Ala
            485                 490                 495
Asn Ile Asn Asp Asp Met Leu Glu Gly Leu Glu Lys Leu Glu Ile Leu
            500                 505                 510
Asp Leu Gln His Asn Asn Leu Ala Arg Leu Trp Lys His Ala Asn Pro
    515                 520                 525
Gly Gly Pro Val Tyr Phe Leu Lys Gly Leu Ser His Leu His Ile Leu
    530                 535                 540
Asn Leu Glu Ser Asn Gly Phe Asp Glu Ile Pro Val Glu Val Phe Lys
545                 550                 555                 560
Asp Leu Ser Glu Leu Lys Ile Ile Asp Leu Gly Leu Asn Asn Leu Asn
            565                 570                 575
Thr Leu Pro Glu Ser Val Phe Asp Asn Gln Val Ser Leu Lys Ser Leu
            580                 585                 590
Asn Leu Gln Lys Asn Leu Ile Thr Ser Val Glu Lys Lys Val Phe Gly
    595                 600                 605
Pro Ala Phe Arg Asn Leu Ser Asn Leu Asp Met Arg Phe Asn Pro Phe
    610                 615                 620
Asp Cys Thr Cys Glu Ser Ile Ala Trp Phe Val Asn Trp Ile Asn Lys
625                 630                 635                 640
Thr His Ala Asn Ile Pro Glu Leu Ser Ser His Tyr Leu Cys Asn Thr
            645                 650                 655
Pro Pro His Tyr His Gly Phe Pro Val Arg Leu Phe Asp Thr Ser Ser
            660                 665                 670
Cys Lys Asp Ser Ala Pro Phe Glu Leu Leu Phe Met Ile Asn Thr Ser
    675                 680                 685
Ile Leu Leu Ile Phe Ile Phe Val Leu Leu Ile His Phe Glu Gly
    690                 695                 700
Trp Arg Ile Ser Phe Tyr Trp Asn Val Ser Val His Arg Val Leu Gly
705                 710                 715                 720
Phe Arg Glu Ile Asp Arg Gln Thr Glu Gln Phe Glu Tyr Ala Ala Tyr
            725                 730                 735
Ile Ile His Ala His Lys Asp Lys Asp Trp Val Trp Glu His Phe Ser
```

```
                        740                 745                 750
Ser Met Glu Lys Glu Asp Gln Ser Leu Lys Phe Cys Leu Glu Glu Arg
            755                 760                 765

Asp Phe Glu Ala Gly Val Phe Glu Leu Glu Ala Ile Val Asn Ser Ile
        770                 775                 780

Lys Arg Ser Arg Lys Ile Ile Phe Ile Ile Thr His His Leu Leu Lys
785                 790                 795                 800

Asp Pro Leu Cys Lys Arg Phe Lys Val His His Ala Val Gln Gln Ala
                805                 810                 815

Ile Glu Gln Asn Leu Asp Ser Ile Ile Leu Ile Phe Leu Glu Glu Ile
            820                 825                 830

Pro Asp Tyr Lys Leu Asn His Ala Leu Cys Leu Arg Arg Gly Met Phe
        835                 840                 845

Lys Ser His Cys Ile Leu Asn Trp Pro Val Gln Lys Glu Arg Ile Gly
850                 855                 860

Ala Phe His His Lys Leu Gln Val Ala Leu Gly Ser Lys Asn Ser Val
865                 870                 875                 880

His

<210> SEQ ID NO 10
<211> LENGTH: 904
<212> TYPE: PRT
<213> ORGANISM: Papio cynocephalus

<400> SEQUENCE: 10

Met Arg Gln Thr Leu Pro Tyr Ile Tyr Phe Trp Trp Gly Leu Leu Pro
1               5                   10                  15

Phe Gly Met Leu Cys Ala Ser Ser Thr Asn Lys Cys Thr Val Ser Gln
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ile Leu
65                  70                  75                  80

Asp Val Gly Phe Asn Ser Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Ser Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Leu Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Leu
    210                 215                 220

Gly Leu Phe Leu Asn Asn Val Gln Leu Gly Pro Ser Leu Thr Glu Lys
225                 230                 235                 240
```

```
Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser His Asn Asn Leu Asn Val
                275                 280                 285

Ile Gly Asn Asp Ser Phe Val Trp Leu Pro His Leu Glu Tyr Phe Phe
290                 295                 300

Leu Glu Tyr Asn Asn Ile Gln His Leu Leu Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
                340                 345                 350

Trp Leu Thr Cys Leu Glu His Leu Asn Met Glu Asp Asn Asp Ile Ser
                355                 360                 365

Gly Ile Lys Ser Asn Met Phe Thr Gly Leu Ile Asn Leu Lys Tyr Leu
370                 375                 380

Ser Leu Ser Asn Ser Phe Thr Ser Leu Gln Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Gly Ala Phe Ser Trp Leu Gly His
                420                 425                 430

Leu Glu Val Leu Asp Leu Gly Leu Asn Glu Ile Gly Gln Glu Leu Thr
                435                 440                 445

Gly Gln Glu Trp Ser Gly Leu Glu Asn Ile Phe Glu Ile Tyr Leu Ser
            450                 455                 460

Tyr Asn Lys Tyr Leu Gln Leu Thr Lys Asn Ser Phe Ala Leu Val Arg
465                 470                 475                 480

Ser Leu Gln Arg Leu Met Leu Arg Arg Val Ala Leu Lys Asn Val Asp
                485                 490                 495

Cys Ser Pro Ser Pro Phe Gln Pro Leu Gly Asn Leu Thr Ile Leu Asp
            500                 505                 510

Leu Ser Asn Asn Asn Ile Ala Asn Ile Asn Asp Asp Met Leu Glu Gly
            515                 520                 525

Leu Glu Lys Leu Glu Ile Leu Asp Leu Gln His Asn Asn Leu Ala Arg
        530                 535                 540

Leu Trp Lys His Ala Asn Pro Gly Gly Pro Val Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Ser Glu Leu Lys Ile Ile Asp
            580                 585                 590

Leu Gly Leu Asn Asn Leu Asn Thr Leu Pro Glu Ser Val Phe Asp Asn
            595                 600                 605

Gln Val Ser Leu Lys Ser Leu Asn Leu Gln Lys Asn Leu Ile Thr Ser
            610                 615                 620

Val Glu Lys Lys Val Phe Gly Pro Ala Phe Arg Asn Leu Ser Asn Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Lys Thr His Ala Asn Ile Pro Glu Leu Ser
```

```
                660               665               670
Ser His Tyr Leu Cys Asn Thr Pro Pro His Tyr His Gly Phe Pro Val
                    675               680               685
Arg Leu Phe Asp Thr Ser Ser Cys Lys Asp Ser Ala Pro Phe Glu Leu
            690               695               700
Leu Phe Met Ile Asn Thr Ser Ile Leu Leu Ile Phe Ile Phe Val Val
705               710               715               720
Leu Leu Ile His Phe Glu Gly Trp Arg Ile Ser Phe Tyr Trp Asn Val
                    725               730               735
Ser Val His Arg Val Leu Gly Phe Arg Glu Ile Asp Arg Gln Thr Glu
                740               745               750
Gln Phe Glu Tyr Ala Ala Tyr Ile Ile His Ala His Lys Asp Lys Asp
            755               760               765
Trp Val Trp Glu His Phe Ser Ser Met Glu Lys Glu Asp Gln Ser Leu
            770               775               780
Lys Phe Cys Leu Glu Glu Arg Asp Phe Glu Ala Gly Val Phe Glu Leu
785               790               795               800
Glu Ala Ile Val Asn Ser Ile Lys Arg Ser Arg Lys Ile Ile Phe Ile
                    805               810               815
Ile Thr His His Leu Leu Lys Asp Pro Leu Cys Lys Arg Phe Lys Val
                820               825               830
His His Ala Val Gln Gln Ala Ile Glu Gln Asn Leu Asp Ser Ile Ile
            835               840               845
Leu Ile Phe Leu Glu Glu Ile Pro Asp Tyr Lys Leu Asn His Ala Leu
            850               855               860
Cys Leu Arg Arg Gly Met Phe Lys Ser His Cys Ile Leu Asn Trp Pro
865               870               875               880
Val Gln Lys Glu Arg Ile Gly Ala Phe His His Lys Leu Gln Val Ala
                    885               890               895
Leu Gly Ser Lys Asn Ser Val His
                900

<210> SEQ ID NO 11
<211> LENGTH: 2747
<212> TYPE: DNA
<213> ORGANISM: Papio cynocephalus

<400> SEQUENCE: 11
catgagacag actttgcctt atatctactt ttggtgggga cttttgccct ttgggatgct    60
gtgtgcatcc tccaccaaca aatgcactgt tagccaagaa gttgctgact gcagccacct   120
gaagttaact caggtacccg atgatctccc cacaaacata acagtgttga atcttaccca   180
taatcaactc aggagattac cagctgccaa ttttacaaga tatagccaac taactatctt   240
ggatgtagga tttaactcca tctcaaaact ggagccagaa ttgtgccaaa aacttcccat   300
gttaaaagtt ttgaacctcc agcacaatga gctatctcaa cttctgata aaacctttgc   360
cttctgcacg aatttgacgg aactccatct catgtccaac tcaatccaga aaattaaaag   420
taatcccttt gtaaagcaga agaatttaat cacattagat ctgtctcata atggcttgtc   480
atctacaaaa ttaggaactc aggttcagct ggaaaatctc caagagcttc tattatcaaa   540
caataaaatc caagcgctaa aaagtgaaga acttgatatc cttgccaatt catctttaaa   600
aaagttagag ttatcatcga atcaaattaa agagttttct ccagggtgtt tcacgcaat    660
tggaagatta ttgggcctct ttctgaacaa cgtccagctg ggtccagcc tcacagaaa    720
gctatgtttg gaattagcaa acacaagcat tcggaatctg tctctgagta acagccagct   780
```

```
gtccaccacc agcaatacaa ctttcttggg actaaagtgg acaaacctca ctatgctcga      840
tctttcccac aacaacttaa atgtgattgg taacgattcc tttgtttggc ttccacatct      900
agaatatttc ttcctggagt ataataatat acagcatttg ctctctcact ctttgcacgg      960
gcttttcaat gtgcggtacc tgaatttgaa acggtctttt actaaacaaa gtatttccct     1020
tgcttcgctc cccaagattg atgatttttc ttttcagtgg ctaacatgtt tggagcacct     1080
taacatggaa gataatgata tttcaggtat aaaaagcaat atgttcacag gattgataaa     1140
cctgaaatac ttaagtctat ccaactcctt tacaagtttg caaactttga caaatgaaac     1200
atttgtatca cttgctcatt ctcccttaca catactcaac ctaaccaaga ataaaatctc     1260
aaaaatagag agtggtgcct tctcttggtt gggccaccta aagtacttg acctgggcct     1320 taatgaaatt gggcaagaac tcacaggcca ggaatggagt ggtctagaaa atattttcga     1380
aatctatctt tcctacaaca agtacctgca actgactaag aactcctttg ccttggtccg     1440
aagccttcaa cgactgatgc tccgaagggt ggcccttaaa aatgtggatt gctctccttc     1500
accattccag cctcttggta acctgaccat tctggatcta agcaacaaca acatagccaa     1560
cataaatgat gacatgttgg aaggtcttga gaaactagaa attctggatt tgcagcataa     1620
caacttagca cggctctgga acacgcaaa ccctggtggt cctgtttatt tcctaaaagg     1680
tctgtctcac ctccacatcc ttaacttgga gtctaatggc tttgacgaga tcccagttga     1740
ggtcttcaag gatttatctg aactaaagat cattgattta ggattgaata atttaaacac     1800
acttccagag tctgtctttg ataatcaggt gtctctaaag tcattgaacc ttcagaagaa     1860
tctcataaca tcagttgaga agaaggtttt tgggccagct ttcaggaacc tgagtaactt     1920
agatatgcgc tttaatccct tgattgcac atgtgaaagt atcgcctggt tgttaactg      1980 gattaacaag acccatgcca acatccctga gctgtcaagc cactacctt gcaacactcc     2040 acctcactat catgggttcc cagtgagact ttttgacaca tcatcctgca agacagtgc     2100 ccccttttgaa ctccttttca tgatcaatac cagtatcctg ttgattttta tctttgttgt     2160
acttctcatc cactttgagg gctgaggat atctttttac tggaatgttt cagtacatcg     2220
agttcttggt ttcagagaaa tagacagaca gacagaacag tttgaatatg cagcatatat     2280
aattcacgcc cataaagata aggattgggt ctgggaacat ttctcttcaa tggaaaagga     2340
agaccaatct ctcaaatttt gtctggaaga aagggacttt gaggcaggtg ttttgaact     2400 ggaagcaatt gttaacagca tcaaaagaag cagaaaaatt attttttatta taacacacca     2460 tctattaaaa gacccattat gcaaaagatt caaggtacat catgccgttc aacaagctat     2520
tgaacaaaat ctggattcca ttatattgat tttccttgag gagattccag attataaact     2580
gaaccatgca ctctgtttga agaggaat gttaaatct cactgcatct tgaactggcc     2640
agttcagaaa gaacggatag gtgccttca tcataaactg caagtagcac ttggatccaa     2700
aaactcagta cattaaattt atttaaatat tcaattagca aaggaga                   2747
```

<210> SEQ ID NO 12
<211> LENGTH: 2712
<212> TYPE: DNA
<213> ORGANISM: Homo sapiens

<400> SEQUENCE: 12

```
atgagacaga ctttgccttg tatctacttt tgggggggcc ttttgcccctt tgggatgctg       60 tgtgcatcct ccaccaccaa gtgcactgtt agccatgaag ttgctgactg cagccacctg      120
aagttgactc aggtacccga tgatctaccc acaaacataa cagtgttgaa ccttacccat      180
```

```
aatcaactca gaagattacc agccgccaac ttcacaaggt atagccagct aactagcttg    240
gatgtaggat ttaacaccat ctcaaaactg gagccagaat tgtgccagaa acttcccatg    300
ttaaaagttt tgaacctcca gcacaatgag ctatctcaac tttctgataa aaccttttgcc   360 ttctgcacga atttgactga actccatctc atgtccaact caatccagaa aattaaaaat    420 aatcccttttg tcaagcagaa gaatttaatc acattagatc tgtctcataa tggcttgtca   480
tctacaaaat taggaactca ggttcagctg gaaaatctcc aagagcttct attatcaaac    540
aataaaattc aagcgctaaa aagtgaagaa ctggatatct ttgccaattc atcttttaaaa   600 aaattagagt tgtcatcgaa tcaaattaaa gagttttctc cagggtgttt tcacgcaatt    660
ggaagattat ttggcctctt tctgaacaat gtccagctgg gtcccagcct tacagagaag    720
ctatgtttgg aattagcaaa cacaagcatt cggaatctgt ctctgagtaa cagccagctg    780
tccaccacca gcaatacaac tttcttggga ctaaagtgga caaatctcac tatgctcgat    840
cttccctaca caacttaaa tgtggttggt aacgattcct ttgcttggct ccacaacta      900 gaatatttct cctagagta taataatata cagcatttgt tttctcactc tttgcacggg    960
cttttcaatg tgaggtacct gaatttgaaa cggtctttta ctaaacaaag tatttccctt   1020
gcctcactcc ccaagattga tgattttctt tttcagtggc taaaatgttt ggagcacctt   1080
aacatggaag ataatgatat ccaggcata aaaagcaata tgttcacagg attgataaac    1140
ctgaaatact taagtctatc caactccttt acaagtttgc gaactttgac aaatgaaaca   1200
tttgtatcac ttgctcattc tcccttacac atactcaacc taaccaagaa taaaatctca   1260
aaaatagaga gtgatgcttt ctcttggttg ggccacctag aagtacttga cctgggcctt   1320
aatgaaattg gcaagaact cacaggccag gaatggagag gtctagaaaa tattttcgaa    1380
atctatcttt cctacaacaa gtacctgcag ctgactagga actcctttgc cttggtccca   1440
agccttcaac gactgatgct ccgaagggtg gcccttaaaa atgtggatag ctctccttca   1500
ccattccagc ctcttcgtaa cttgaccatt ctggatctaa gcaacaacaa catagccaac   1560
ataaatgatg acatgttgga gggtcttgag aaactagaaa ttctcgattt gcagcataac   1620
aacttagcac ggctctggaa acacgcaaac cctggtggtc ccatttattt cctaaagggt   1680
ctgtctcacc tccacatcct taacttggag tccaacggct tgacgagat cccagttgag   1740 gtcttcaagg atttatttga actaaagatc atcgatttag gattgaataa tttaaacaca   1800
cttccagcat ctgtctttaa taatcaggtg tctctaaagt cattgaacct tcagaagaat   1860
ctcataacat ccgttgagaa gaaggttttc gggccagctt tcaggaacct gactgagtta   1920
gatatgcgct ttaatccctt tgattgcacg tgtgaaagta ttgcctggtt tgttaattgg   1980
attaacgaga cccataccaa catccctgag ctgtcaagcc actacctttg caacactcca   2040
cctcactatc atgggttccc agtgagactt tttgatacat catcttgcaa agacagtgcc   2100 cccttttgaac tcttttttcat gatcaatacc agtatcctgt tgatttttat ctttattgta   2160
cttctcatcc actttgaggg ctggaggata tcttttttatt ggaatgtttc agtacatcga   2220
gttcttggtt tcaaagaaat agacagacag acagaacagt ttgaatatgc agcatatata   2280
attcatgcct ataaagataa ggattgggtc tgggaacatt tctcttcaat ggaaaaggaa   2340
gaccaatctc tcaaattttg tctggaagaa agggactttg aggcgggtgt ttttgaacta   2400
gaagcaattg ttaacagcat caaaagaagc agaaaaatta tttttgttat aacacaccat   2460
ctattaaaag acccattatg caaaagattc aaggtacatc atgcagttca acaagctatt   2520
gaacaaaatc tggattccat tatattggtt ttccttgagg agattccaga ttataaactg   2580
```

```
aaccatgcac tctgtttgcg aagaggaatg tttaaatctc actgcatctt gaactggcca   2640
gttcagaaag aacggatagg tgcctttcgt cataaattgc aagtagcact tggatccaaa   2700
aactctgtac at                                                       2712
```

<210> SEQ ID NO 13
<211> LENGTH: 904
<212> TYPE: PRT
<213> ORGANISM: Homo sapiens

<400> SEQUENCE: 13

```
Met Arg Gln Thr Leu Pro Cys Ile Tyr Phe Trp Gly Gly Leu Leu Pro
 1               5                  10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
        50                  55                  60

Arg Leu Pro Ala Ala Asn Phe Thr Arg Tyr Ser Gln Leu Thr Ser Leu
 65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
            115                 120                 125

His Leu Met Ser Asn Ser Ile Gln Lys Ile Lys Asn Asn Pro Phe Val
        130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
                180                 185                 190

Ile Phe Ala Asn Ser Ser Leu Lys Lys Leu Glu Leu Ser Ser Asn Gln
            195                 200                 205

Ile Lys Glu Phe Ser Pro Gly Cys Phe His Ala Ile Gly Arg Leu Phe
        210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
                260                 265                 270

Trp Thr Asn Leu Thr Met Leu Asp Leu Ser Tyr Asn Asn Leu Asn Val
            275                 280                 285

Val Gly Asn Asp Ser Phe Ala Trp Leu Pro Leu Glu Tyr Phe Phe
        290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350
```

-continued

```
Trp Leu Lys Cys Leu Glu His Leu Asn Met Glu Asp Asn Asp Ile Pro
            355                 360                 365
Gly Ile Lys Ser Asn Met Phe Thr Gly Leu Ile Asn Leu Lys Tyr Leu
            370                 375                 380
Ser Leu Ser Asn Ser Phe Thr Ser Leu Arg Thr Leu Thr Asn Glu Thr
385                 390                 395                 400
Phe Val Ser Leu Ala His Ser Pro Leu His Ile Leu Asn Leu Thr Lys
                405                 410                 415
Asn Lys Ile Ser Lys Ile Glu Ser Asp Ala Phe Ser Trp Leu Gly His
                420                 425                 430
Leu Glu Val Leu Asp Leu Gly Leu Asn Glu Ile Gly Gln Glu Leu Thr
            435                 440                 445
Gly Gln Glu Trp Arg Gly Leu Glu Asn Ile Phe Glu Ile Tyr Leu Ser
        450                 455                 460
Tyr Asn Lys Tyr Leu Gln Leu Thr Arg Asn Ser Phe Ala Leu Val Pro
465                 470                 475                 480
Ser Leu Gln Arg Leu Met Leu Arg Arg Val Ala Leu Lys Asn Val Asp
                485                 490                 495
Ser Ser Pro Ser Pro Phe Gln Pro Leu Arg Asn Leu Thr Ile Leu Asp
            500                 505                 510
Leu Ser Asn Asn Asn Ile Ala Asn Ile Asn Asp Asp Met Leu Glu Gly
            515                 520                 525
Leu Glu Lys Leu Glu Ile Leu Asp Leu Gln His Asn Asn Leu Ala Arg
            530                 535                 540
Leu Trp Lys His Ala Asn Pro Gly Gly Pro Ile Tyr Phe Leu Lys Gly
545                 550                 555                 560
Leu Ser His Leu His Ile Leu Asn Leu Glu Ser Asn Gly Phe Asp Glu
                565                 570                 575
Ile Pro Val Glu Val Phe Lys Asp Leu Phe Glu Leu Lys Ile Ile Asp
            580                 585                 590
Leu Gly Leu Asn Asn Leu Asn Thr Leu Pro Ala Ser Val Phe Asn Asn
            595                 600                 605
Gln Val Ser Leu Lys Ser Leu Asn Leu Gln Lys Asn Leu Ile Thr Ser
        610                 615                 620
Val Glu Lys Lys Val Phe Gly Pro Ala Phe Arg Asn Leu Thr Glu Leu
625                 630                 635                 640
Asp Met Arg Phe Asn Pro Phe Asp Cys Thr Cys Glu Ser Ile Ala Trp
                645                 650                 655
Phe Val Asn Trp Ile Asn Glu Thr His Thr Asn Ile Pro Glu Leu Ser
                660                 665                 670
Ser His Tyr Leu Cys Asn Thr Pro Pro His Tyr His Gly Phe Pro Val
            675                 680                 685
Arg Leu Phe Asp Thr Ser Ser Cys Lys Asp Ser Ala Pro Phe Glu Leu
        690                 695                 700
Phe Phe Met Ile Asn Thr Ser Ile Leu Leu Ile Phe Ile Phe Ile Val
705                 710                 715                 720
Leu Leu Ile His Phe Glu Gly Trp Arg Ile Ser Phe Tyr Trp Asn Val
                725                 730                 735
Ser Val His Arg Val Leu Gly Phe Lys Glu Ile Asp Arg Gln Thr Glu
            740                 745                 750
Gln Phe Glu Tyr Ala Ala Tyr Ile Ile His Ala Tyr Lys Asp Lys Asp
        755                 760                 765
Trp Val Trp Glu His Phe Ser Ser Met Glu Lys Glu Asp Gln Ser Leu
```

```
                770                 775                 780
Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900
```

```
<210> SEQ ID NO 14
<211> LENGTH: 24
<212> TYPE: DNA
<213> ORGANISM: Artificial Sequence
<220> FEATURE:
<223> OTHER INFORMATION: Human Oligos used for RT-PCR of baboon TLR3

<400> SEQUENCE: 14
gatctgtctc ataatggctt gtca                                          24

<210> SEQ ID NO 15
<211> LENGTH: 23
<212> TYPE: DNA
<213> ORGANISM: Artificial Sequence
<220> FEATURE:
<223> OTHER INFORMATION: Human Oligos used for RT-PCR of baboon TLR3

<400> SEQUENCE: 15
gtttatcaat cctgtgaaca tat                                           23

<210> SEQ ID NO 16
<211> LENGTH: 21
<212> TYPE: DNA
<213> ORGANISM: Artificial Sequence
<220> FEATURE:
<223> OTHER INFORMATION: Human Oligos Incorporating Start and Stop Codon
      of the TLR3 Gene

<400> SEQUENCE: 16
atgagacaga ctttgccttg t                                             21

<210> SEQ ID NO 17
<211> LENGTH: 21
<212> TYPE: DNA
<213> ORGANISM: Artificial Sequence
<220> FEATURE:
<223> OTHER INFORMATION: Baboon Oligos Designed Using Previously Cloned
      portion of Baboon TLR3 as template

<400> SEQUENCE: 17
caaatgctgt atattattat a                                             21

<210> SEQ ID NO 18
<211> LENGTH: 19
<212> TYPE: DNA
```

```
<213> ORGANISM: Artificial Sequence
<220> FEATURE:
<223> OTHER INFORMATION: Baboon Oligos Designed Using Previously Cloned
      portion of Baboon TLR3 as template

<400> SEQUENCE: 18
gttagagtta tcatcgaat                                                  19

<210> SEQ ID NO 19
<211> LENGTH: 21
<212> TYPE: DNA
<213> ORGANISM: Artificial Sequence
<220> FEATURE:
<223> OTHER INFORMATION: Human Oligos Incorporating Start and Stop Codon
      of the TLR3 Gene

<400> SEQUENCE: 19
ttaatgtaca gagttttgg a                                                21

<210> SEQ ID NO 20
<211> LENGTH: 13
<212> TYPE: DNA
<213> ORGANISM: Artificial Sequence
<220> FEATURE:
<223> OTHER INFORMATION: Oligos Designed to Amplify the 5' portion of
      Baboon TLR3. PCR Product Encompasses UTR and
      Translated Region

<400> SEQUENCE: 20
catccaacag aat                                                        13

<210> SEQ ID NO 21
<211> LENGTH: 21
<212> TYPE: DNA
<213> ORGANISM: Artificial Sequence
<220> FEATURE:
<223> OTHER INFORMATION: Oligos Designed to Amplify the 5' portion of
      Baboon TLR3. PCR Product Encompasses UTR and
      Translated Region

<400> SEQUENCE: 21
caaatgctgt atattattat a                                               21

<210> SEQ ID NO 22
<211> LENGTH: 21
<212> TYPE: DNA
<213> ORGANISM: Artificial Sequence
<220> FEATURE:
<223> OTHER INFORMATION: Oligos Designed to Amplify the 3' portion of
      Baboon TLR3. PCR Product Encompasses UTR and
      Translated Region

<400> SEQUENCE: 22
ttgaatatgc agcatatata a                                               21

<210> SEQ ID NO 23
<211> LENGTH: 22
<212> TYPE: DNA
<213> ORGANISM: Artificial Sequence
<220> FEATURE:
<223> OTHER INFORMATION: Oligos Designed to Amplify the 3' portion of
      Baboon TLR3. PCR Product Encompasses UTR and
      Translated Region

<400> SEQUENCE: 23 aacttttaa attgagaaag tt                                               22

<210> SEQ ID NO 24
```

```
<211> LENGTH: 45
<212> TYPE: DNA
<213> ORGANISM: Artificial Sequence
<220> FEATURE:
<223> OTHER INFORMATION: Oligos Designed to Amplify Coding Sequence and
      Incorporate Restriction Sites for pBETH Expression
      Construct Subcloning

<400> SEQUENCE: 24
attattgcgg ccgccaccat gagacagact ttgccttgta tctac            45

<210> SEQ ID NO 25
<211> LENGTH: 41
<212> TYPE: DNA
<213> ORGANISM: Artificial Sequence
<220> FEATURE:
<223> OTHER INFORMATION: Oligos Designed to Amplify Coding Sequence and
      Incorporate Restriction Sites for pBETH Expression
      Construct Subcloning

<400> SEQUENCE: 25
taataactcg agttaatgta cagagttttt ggatccaagt g                41
```